United States Patent
Beight et al.

(10) Patent No.: US 6,730,694 B1
(45) Date of Patent: May 4, 2004

(54) SPLA$_2$ INHIBITORS

(75) Inventors: Douglas Wade Beight, Frankfort, IN (US); John Michael Morin, Jr., Brownsburg, IN (US); Jason Scott Sawyer, Indianapolis, IN (US); Edward C R Smith, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/332,480

(22) PCT Filed: Jul. 20, 2001

(86) PCT No.: PCT/US01/21106

§ 371 (c)(1),
(2), (4) Date: Jan. 7, 2003

(87) PCT Pub. No.: WO02/12249

PCT Pub. Date: Feb. 14, 2002

(51) Int. Cl.[7] .................... A61K 31/407; C07D 495/04
(52) U.S. Cl. ....................................... 514/412; 548/453
(58) Field of Search ........................... 548/453; 514/412

(56) References Cited

U.S. PATENT DOCUMENTS

| | | | | |
|---|---|---|---|---|
| 4,567,196 A | * | 1/1986 | Wierzbicki | 514/422 |
| 4,608,384 A | * | 8/1986 | Wierzbicki et al. | 514/412 |

FOREIGN PATENT DOCUMENTS

| | | |
|---|---|---|
| EP | 0 114 014 | 7/1984 |
| EP | 0 675 110 | 10/1995 |
| FR | 2 564 467 | 11/1985 |
| FR | 2 565 981 | 12/1985 |
| WO | WO 98/25609 | 6/1998 |
| WO | WO 99/09978 | 3/1999 |
| WO | WO 99/16453 | 4/1999 |
| WO | WO 99/40914 | 8/1999 |
| WO | WO 99/51605 | 10/1999 |
| WO | WO 99/59999 | 11/1999 |
| WO | WO 00/00201 | 1/2000 |

\* cited by examiner

*Primary Examiner*—Fiona T. Powers
(74) *Attorney, Agent, or Firm*—Francis O. Ginah

(57) ABSTRACT

A class of novel substituted pyrrole is disclosed together with the use of such compounds for inhibiting sPLA$_2$ mediated release of fatty acids for treatment of Inflammatory Diseases such as septic shock.

23 Claims, 1 Drawing Sheet

SPLA₂ INHIBITORS

FIELD OF THE INVENTION

Figure 1:
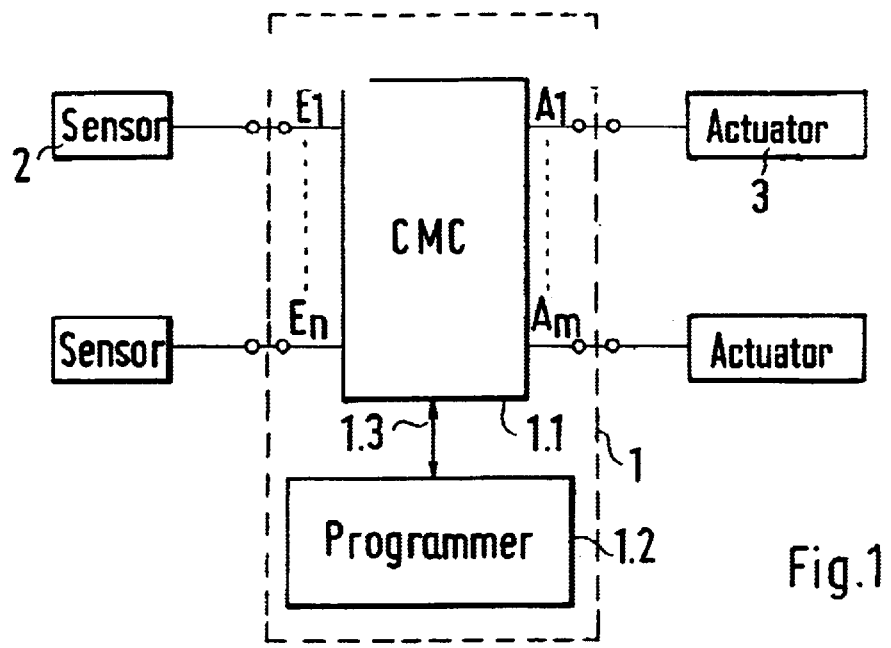

This invention relates to novel substituted pyrrole compounds useful for Inflammatory Diseases.

BACKGROUND OF THE INVENTION

The structure and physical properties of human non-pancreatic secretory phospholipase A₂ (hereinafter called, "sPLA₂") has been thoroughly described in two articles, namely, "Cloning and Recombinant Expression of Phospholipase A₂ Present in Rheumatoid Arthritic Synovial Fluid" by Seilhamer, Jeffrey J.; Pruzanski, Waldemar; Vadas Peter, Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase A₂" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that sPLA₂ is a rate limiting enzyme in the arachidonic acid cascade which hydrolyzes membrane phospholipids. Thus, it is important to develop compounds which inhibit sPLA₂ mediated release of fatty acids (e.g., arachidonic acid). Such compounds would be of value in general treatment of conditions induced and/or maintained by overproduction of sPLA₂; such as sepsis or rheumatoid arthritis.

It is desirable to develop new compounds and treatments for sPLA₂ induced diseases.

SUMMARY OF THE INVENTION

This invention provides novel substituted pyrrole compounds having potent and selective effectiveness as inhibitors of mammalian sPLA₂.

This invention is also the use of novel substituted pyrrole compounds useful in the treatment and prevention of Inflammatory Diseases.

This invention is also the use of novel substituted pyrrole compounds to inhibit mammalian sPLA₂ mediated release of fatty acids.

This invention is also a pharmaceutical composition containing any of the substituted pyrrole compounds of the invention.

I. Definitions

The term, "Inflammatory Diseases" refers to diseases such as inflammatory bowel disease, sepsis, septic shock, adult respiratory distress syndrome, pancreatitis, trauma-induced shock, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non particular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit sPLA₂ mediated release of fatty acid and to thereby inhibit or prevent the arachidonic acid cascade and its deleterious products.

The term, "substituted pyrrole nucleus" as used herein refers to a nucleus (having numbered positions) with the structural formula (X):

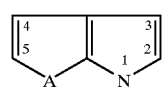

(X)

wherein A is O, NR, SO₂, SO, or S.

The substituted pyrrole compounds of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, sec-butyl, n-pentyl, and n-hexyl.

The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo. The term, heterocyclic radical, refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiopheneyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, spiro[5.5]undecanyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, dibenzylyl and related dibenzylyl homologues represented by the formula (a):

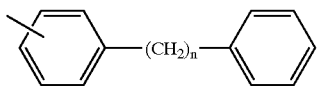

(a)

where n is a number from 1 to 8.

The terms, "non-interfering substituent", and "non-interfering group" refer to radicals suitable for substitution at positions 4, 5, 6 and/or 7 of the substituted pyrrole nucleus and on other nucleus positions or substituents (as hereinafter described for Formula I), and radicals suitable for substitution on the heterocyclic radical and carbocyclic radical as defined above. Illustrative non-interfering radicals are $C_1$–$C_8$ alkyl, $C_2$–$C_8$ alkenyl, $C_2$–$C_8$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_8$ alkoxy, $C_2$–$C_8$ alkenyloxy, $C_2$–$C_8$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_8$ alkylsulfinyl, $C_1$–$C_8$ alkylsulfonyl, $C_2$–$C_8$ haloalkoxy, $C_1$–$C_8$ haloalkylsulfonyl, $C_2$–$C_8$ haloalkyl, $C_1$–$C_8$ hydroxyalkyl, —C(O)O($C_1$–$C_8$ alkyl), —$(CH_2)_n$—O—($C_1$–$C_8$ alkyl), benzyloxy, phenoxy, phenylthio, —($CONHSO_2R$), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and carbonyl; where n is from 1 to 8 and R is $C_1$–$C_8$ alkyl.

The term, "organic substituent" refers to a monovalent radical consisting of carbon and hydrogen with or without oxygen, nitrogen, sulfur, halogen, or other elements. Illustrative organic substituents are $C_1$–$C_8$ alkyl, aryl, $C_7$–$C_{14}$ aralkyl, $C_7$–$C_{14}$ alkaryl, $C_3$–$C_8$ cycloalkyl, $C_1$–$C_8$ alkoxyalkyl and these groups substituted with halogen, —$CF_3$, —OH, $C_1$–$C_8$ alkyl, amino, carbonyl, and —CN.

The term "substituted group" is an organic group substituted with one or more non-interfering substituents.

The term, "(acidic group)" means an organic group which when attached to a substituted pyrrole nucleus at positions 4 or 5, through suitable linking atoms (hereinafter defined as the "acid linker"), acts as a proton donor capable of hydrogen bonding. Illustrative of an (acidic group) are the following:

-5-tetrazolyl,

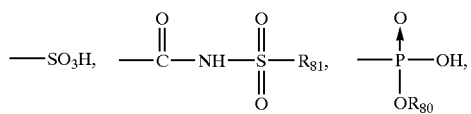

-continued

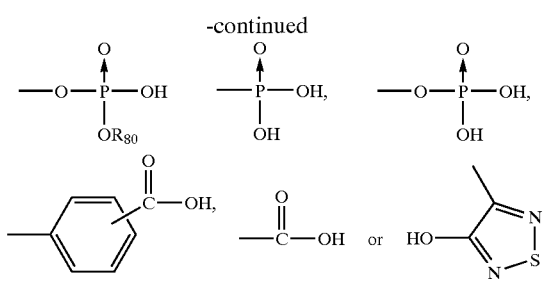

where n is 1 to 8, $R_{80}$ is a metal or $C_1$–$C_8$ and $R_{81}$ is an organic substituent or —$CF_3$.

The words, "acid linker" refer to a divalent linking group symbolized as, —($L_a$)—, which has the function of joining the 4 or 5 position of the substituted pyrrole nucleus to an acidic group in the general relationship:

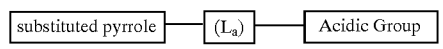

The words, "acid linker length", refer to the number of atoms (excluding hydrogen) in the shortest chain of the linking group —($L_a$)— that connects the 4 or 5 position of the substituted pyrrole nucleus with the acidic group. The presence of a carbocyclic ring in —($L_a$)— counts as the number of atoms approximately equivalent to the calculated diameter of the carbocyclic ring. Thus, a benzene or cyclohexane ring in the acid linker counts as 2 atoms in calculating the length of —($L_a$)—. Illustrative acid linker groups are;

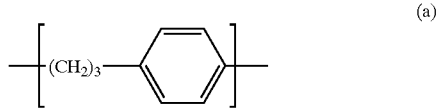
(a)

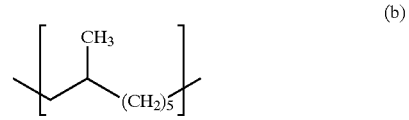
(b)

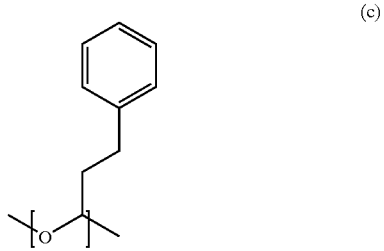
(c)

wherein, groups (a), (b), and (c) have acid linker lengths of 5, 7, and 2, respectively.

The term, "N-hydroxyfunctional amide group" is represented by the formula:

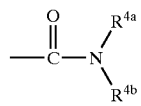

wherein,
$R^{4a}$ is selected from the group consisting of OH, ($C_1$–$C_6$) alkoxy, and aryloxy; and
wherein $R^{4b}$ is hydrogen or an organic substituent selected from the group consisting of $C_1$–$C_8$ alkyl, aryl, $C_7$–$C_{14}$ aralkyl, $C_7$–$C_{14}$ alkaryl, $C_3$–$C_8$ cycloalkyl, $C_1$–$C_8$ alkoxyalkyl and these groups substituted with halogen, —$CF_3$, —OH, $C_1$–$C_8$ alkyl, amino, carbonyl, and —CN.

The phrase, "N-hydroxyfunctional amide linker" refers to a divalent linking group symbolized as, —($L_h$)—, which has the function of joining the 4 position of the substituted pyrrole nucleus to an N-hydroxyfunctional amide group in the general relationship:

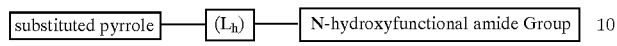

The words, "N-hydroxyfunctional amide linker length", refer to the number of atoms (excluding hydrogen) in the shortest chain of the linking group —($L_h$)— that connects the 4 position of the substituted pyrrole nucleus with the N-hydroxyfunctional amide group. The presence of a carbocyclic ring in —($L_h$)— counts as the number of atoms approximately equivalent to the calculated diameter of the carbocyclic ring. Thus, a benzene or cyclohexane ring in the N-hydroxyfunctional amide linker counts as 2 atoms in calculating the length of —($L_h$)—. Illustrative N-hydroxyfunctional amide linker groups are;

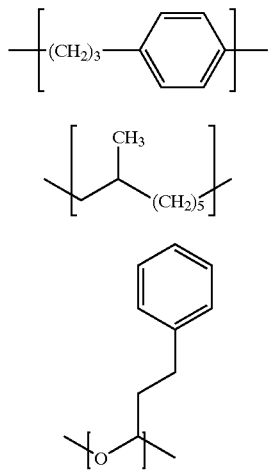

wherein, groups (a), (b), and (c) have N-hydroxyfunctional amide linker lengths of 5, 7, and 2, respectively.

The term, "acylamino acid group" is represented by the formula:

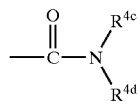

wherein $R^{4c}$ is selected from the group consisting of H, ($C_1$–$C_6$)alkyl, ($C_1$–$C_6$)alkoxy, heteroaryl and aryl, —$CF_3$; and wherein $NR^{4d}$ is an amino acid residue of either a natural or unnatural amino acid with the nitrogen atom being part of the amino group of the amino acid. A typical amino acid is selected from the group comprising isoleucine, valine, phenylalanine, aspartic acid, leucine, glycine, asparagine, cystein, glutamine, glutamic acid, histidine, lysine, methionine, serine, threonine, tryptophan, tyrosine and derivatives thereof. Contemplated within the definition of amino acid are l-proline, d-proline and derivatives thereof.

Also contemplated within the definition of amino acids are peptides, polypeptides and derivatives thereof. The term, "amino acid residue" refers to the portion of the amino acid group coupled at the nitrogen atom of the amino terminus. It is the amino acid less a hydrogen atom from the amino terminus. It is further illustrated as used herein for the amino acid alanine attached at the nitrogen atom as shown below:

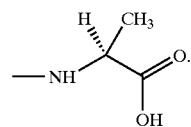

The words, "acylamino acid linker" refer to a divalent linking group symbolized as, —($L_c$)—, which has the function of joining the 4 position of the substituted pyrrole nucleus to an acylamino acid group in the general relationship:

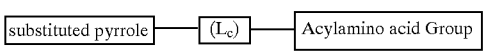

The words, "acylamino acid linker length", refer to the number of atoms (excluding hydrogen) in the shortest chain of the linking group —($L_c$)— that connects the 4 position of the substituted pyrrole nucleus with the acidic group. The presence of a carbocyclic ring in —($L_c$)— counts as the number of atoms approximately equivalent to the calculated diameter of the carbocyclic ring. Thus, a benzene or cyclohexane ring in the acid linker counts as 2 atoms in calculating the length of —($L_c$)—. Illustrative acylamino acid linker groups are;

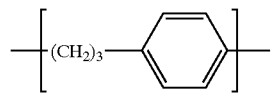

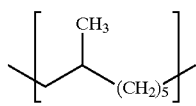

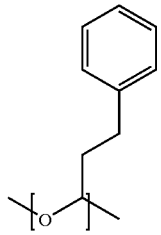

wherein, groups (a), (b), and (c) have acylamino acid linker lengths of 5, 7, and 2, respectively.

As used herein the terms "group", "radical" or "fragment" are synonymous and are intended to indicate functional groups or fragments of molecules attachable to a bond or other fragments of molecules. For example acetamide group represent the acetamide fragment or radical. Structures of groups, radicals or fragments unattached to the substituted pyrrole nucleus have been drawn to show the first line as a connecting bond only, Thus, the group

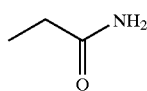

indicates the acetamide radical not the propanamide radical unless otherwise indicated.

The term, "amine", includes primary, secondary and tertiary amines.

The terms, "mammal" and "mammalian" include human and domesticated quadrupeds.

The term, "alkylene chain of 1 or 2 carbon atoms" refers to the divalent radicals, —CH$_2$—CH$_2$— and —CH$_2$—.

The term "group containing 1 to 4 non-hydrogen atom" refers to relatively small groups which form-substituents at the 2 position of the substituted pyrrole nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain no more than 4 non-hydrogen atoms such as —CF$_3$, —Cl, —Br, —NO$_2$, —CN, —SO$_3$; and (ii) groups having hydrogen atoms which contain less than 4 non-hydrogen atoms such as —CH$_3$, —C$_2$H$_5$, and —CH=CH$_2$.

The term "oxime amide" means the radical, —C(=NOR)—C(O)NH$_2$ wherein R is alkyl, aryl, alkylaryl or arylalkyl.

The term "thio-oxime amide" means the radical —C(=NOR)—C(S)—NH$_2$ wherein R is alkyl, aryl, alkylaryl or arylalkyl.

The term "spiro[5.5]undecanyl" refers to the group represented by the formula;

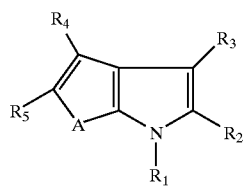

II. The Substituted Pyrrole Compounds of the Invention

The present invention provides novel classes of substituted pyrrole compounds useful as sPLA$_2$ inhibitors for the treatment of Inflammatory Diseases. Classes of substituted pyrrole compounds of this invention include substituted pyrrole glyoxylamide derivatives, substituted pyrrole-3-oxime amide derivatives and substituted pyrrole acetamide derivatives. The compounds of the invention have the general formula (I) or a pharmaceutically acceptable salt, solvate or prodrug thereof;

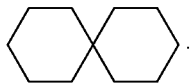

(I)

wherein;
A is O, S, SO, SO$_2$, or NR; and wherein R is a non-interfering substituent;
R$_1$ is selected from groups (a), (b), and (c) wherein;
(a) is C$_7$-C$_{20}$ alkyl, C$_7$-C$_{20}$ haloalkyl, C$_7$-C$_{20}$ alkenyl, C$_7$-C$_{20}$ alkynyl, carbocyclic radical, or heterocyclic radical, or (b) is a member of (a) substituted with one or more independently selected non-interfering substituents; or
(c) is the group —(L$_1$)—R$_{11}$; where, —(L$_1$)— is a divalent linking group of 1 to 8 atoms and where R$_{11}$ is a group selected from (a) or (b),
R$_2$ is hydrogen, or a group containing 1 to 4 non-hydrogen atoms plus any required hydrogen atoms;
R$_3$ is —(L$_3$)— Z, where —(L$_3$)— is a divalent linker group selected from a bond or a divalent group selected from:

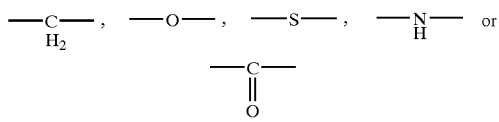

and Z is selected from an amide including acetamide, oxime amide, oxime thioamide, glyoxylamide or a group represented by the formulae,

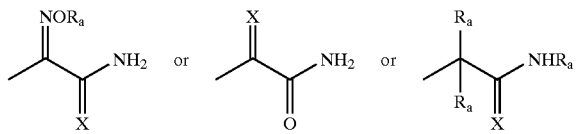

wherein X is oxygen or sulfur, R$_a$ is independently selected from hydrogen, C$_1$-C$_8$ alkyl, aryl, C$_1$-C$_8$ alkaryl, C$_1$-C$_8$ alkoxy, aralkyl and —CN;
R$_4$ is the group hydrogen, or the group —(L$_a$)—(acidic group); wherein —(L$_a$)—, is an acid linker having an acid linker length of 1 to 8;
or the group WR$^{4e}$ wherein W is O, S, or NH, and R$^{4e}$ is a non-interfering substituent;
or the group (L$_c$)—(acylamino acid group); wherein —(L$_c$)—, is an acylamino acid linker having an acylamino acid linker length of 1 to 8;
or the group —(L$_h$)—(N-hydroxyfunctional amide group); wherein —(L$_h$)—, is an N-hydroxyfunctional amide linker having an N-hydroxyfunctional amide linker length of 1 to 8;
R$_5$ is selected from hydrogen, a non-interfering substituent, or the group, —(L$_a$)—(acidic group); wherein —(L$_a$)—, is an acid linker having an acid linker length of 1 to 8;

Preferred Subgroups of Compounds of Formula (I):
Preferred R$_1$ Substituents:
A preferred subclass of compounds of formula (I) are those for which the substituent A is sulfur or oxygen. Most preferred are compounds of formula (I) wherein the substituent A is sulfur.

Another preferred subclass of compounds of formula (I) are those where for R$_1$ the divalent linking group —(L$_1$)— is a group represented by any one of the following formulae (Ia), (Ib), (Ic), (Id), (Ie), or (If):

(Ia)

(Ib)

(Ic)

-continued $$-\underset{H}{N}-\quad \text{or} \tag{Id}$$

$$-\underset{\parallel}{\overset{\parallel}{C}}-\quad \text{or} \tag{Ie}$$

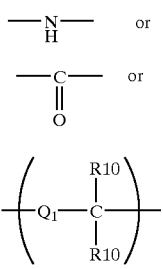 (If)

where $Q_1$ is a bond or any of the divalent groups (Ia), (Ib), (Ic), (Id), (Ie), and (If) and each $R_{10}$ is independently hydrogen, $C_1$–$C_8$ alkyl, $C_1$–$C_8$ haloalkyl or $C_1$–$C_8$ alkoxy.

Particularly preferred as the linking group —($L_1$)— of $R_1$ is an alkylene chain of 1 or 2 carbon atoms, namely, —($CH_2$)— or —($CH_2$—$CH_2$)—.

The preferred group for $R_{11}$ is a substituted or unsubstituted group selected from the group consisting of $C_5$–$C_{14}$ cycloalkyl, $C_5$–$C_{14}$ cycloalkenyl, phenyl, naphthyl, norbornanyl, bicycloheptadienyl, toluyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (a);

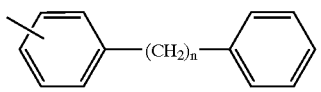 (a)

where n is a number from 1 to 8.

Particularly preferred are compounds wherein for $R_1$ the combined group —($L_1$)—$R_{11}$ is selected from the group consisting of

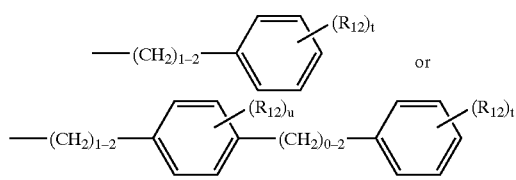

where $R_{12}$ is a radical independently selected from halo, $C_1$–$C_8$ alkyl, $C_1$–$C_8$ alkoxy, —S—($C_1$–$C_8$ alkyl), —O—($C_1$–$C_8$ alkyl) and $C_1$–$C_8$ haloalkyl where t is a number from 0 to 5 and u is a number from 0 to 4 is the group —($L_1$)—$R_{11}$; where, —($L_1$)— is a divalent linking group of 1 to 8 atoms and where $R_{11}$ is a group selected from (a) or (b).

Preferred for $R_{11}$ is —($CH_2$)m—$R^{12}$ wherein m is an integer from 1 to 6, and $R^{12}$ is (d) a group represented by the formula:

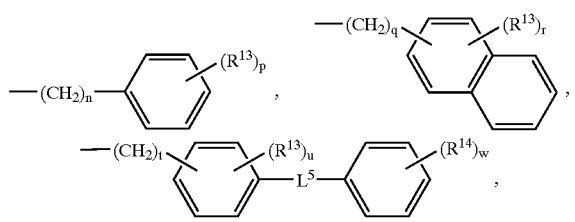

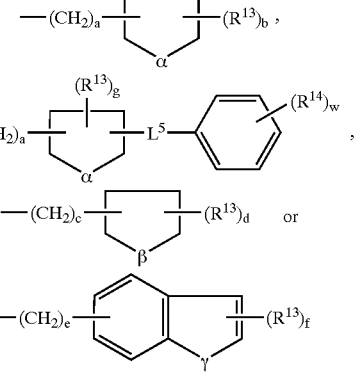

wherein a, c, e, n, q, and t are independently an integer. from 0 to 2, $R^{13}$ and $R^{11}$ are independently selected from a halogen, $C_1$ to $C_8$ alkyl, $C_1$ to $C_8$ alkyloxy, $C_1$ to $C_8$ alkylthio, aryl, heteroaryl, and $C_1$ to $C_8$ haloalkyl, α is an oxygen atom or a sulfur atom, $L^5$ is a bond, —($CH_2$)v—, —C=C—, —CC—, —O—, or —S—, v is an integer from 0 to 2, β is —$CH_2$— or ($CH_2$)$_2$—, γ is an oxygen atom or a sulfur atom, b is an integer from 0 to 3, d is an integer from 0 to 4, f, p, and w are independently an integer from 0 to 5, r is an integer from 0 to 7, and u is an integer from 0 to 4, or is (e) a member of (d) substituted with at least one substituent selected from the group consisting of $C_1$ to $C_6$ alkyl, $C_1$ to $C_8$ alkyloxy, $C_1$ to $C_8$ haloalkyloxy, $C_1$ to $C_8$ haloalkyl, aryl, and a halogen.

Preferred $R_2$ Substituents:

$R_2$ is preferably selected from the group consisting of hydrogen, $C_2$–$C_4$ alkyl, $C_2$–$C_4$ alkenyl, —O—($C_1$–$C_3$ alkyl), —S—($C_1$–$C_3$ alkyl), —$C_3$–$C_4$ cycloalkyl —$CF_3$, halo, —$NO_2$, —CN, —$SO_3$. Particularly preferred $R_2$ groups are selected from hydrogen, methyl, ethyl, propyl, isopropyl, cyclopropyl, —F, —$CF_3$, —Cl, —Br, or —O—$CH_3$.

Preferred $R_3$ Substituents:

A preferred subclass of compounds of formula (I) are those wherein for —($L_3$)— Z, Z is represented by

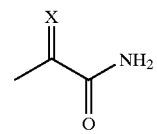

and X is oxygen.

Another preferred subclass of compounds of formula (I) are those wherein Z is an oxime amide group

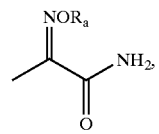

wherein $R_3$ is an oxime amide group and $R_a$ is hydrogen, methyl or ethyl.

Also preferred is a subclass of compounds of formula (I) wherein Z is an acetamide group

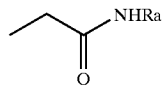

wherein, X is oxygen or sulfur; and $R_a$ is selected from hydrogen, $C_1$–$C_8$ alkyl, aryl, and $C_1$–$C_8$ alkaryl.

For the group $R_3$ it is most preferred that the linking group —($L_3$)— be a bond.

Preferred $R_4$ Substituents:

Another preferred subclass of compounds of formula (I) are those wherein, $R_4$ is the group $WR^{4e}$ wherein W is oxygen, and $R^{4e}$ is a non-interfering substituent independently selected from the group consisting of methyl, ethyl, propyl, isopropyl, thiomethyl, $C_4$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —($CH_2$)$_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —($CH_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and carbonyl; where n is from 1 to 8.

Most preferred as non-interfering substituents are hydrogen, methyl, ethyl, propyl, and isopropyl.

Preferred as the N-hydroxyfunctional amide group in the group $R_4$ is the group:

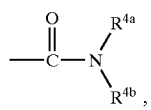

wherein $R^{4a}$ is selected from the group consisting of OH, ($C_1$–$C_6$)alkoxy and aryloxy; and wherein $R^{4b}$ is an organic substituent selected from the group consisting of H, $C_1$–$C_8$ alkyl, aryl, $C_7$–$C_{14}$ aralkyl, $C_7$–$C_{14}$ alkaryl, $C_3$–$C_8$ cycloalkyl, $C_1$–$C_8$ alkoxyalkyl and these groups substituted with halogen, —CF$_3$, —OH, $C_1$–$C_8$ alkyl, amino, carbonyl, and —CN. A more preferred $R^{4a}$ group is selected from the group consisting of —OH, —OCH$_3$ and —OC$_2$H$_5$. A more preferred $R^{4b}$ is selected from the group consisting of H, $C_1$–$C_8$ alkyl, aryl, $C_7$–$C_{14}$ aralkyl, $C_7$–$C_{14}$ alkaryl, $C_3$–$C_8$ cycloalkyl. A most preferred $R^{4b}$ is a group selected from H, CH$_3$, C$_2$H$_5$ and C$_3$H$_7$.

Another preferred subclass of compounds of formula I are those wherein $R_4$ is the group —(Lc)—(acylamino acid group)-, wherein —(Lc)— is an acylamino acid linker with an acylamino acid linker length of 2 or 3, and the "acylamino acid group" is represented by the formula:

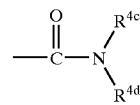

wherein $R^{4c}$ is selected from the group consisting of H, ($C_1$–$C_6$)alkyl, ($C_1$–$C_6$)alkoxy, heteroaryl and aryl, —CF$_3$; and wherein NR$^{4d}$ is an amino acid residue of either a natural or unnatural amino acid with the nitrogen atom being part of the amino group of the amino acid; and wherein the amino acid residue is derived from an amino acid selected from the group comprising isoleucine, valine, phenylalanine, aspartic acid, leucine, glycine, asparagine, cystein, glutamine, glutamic acid, histidine, lysine, methionine, serine, threonine, tryptophan, tyrosine and derivatives thereof.

Preferred $R_5$ Substituents:

A preferred acid linker, —($L_a$)—, for $R_5$ is selected from the group consisting of;

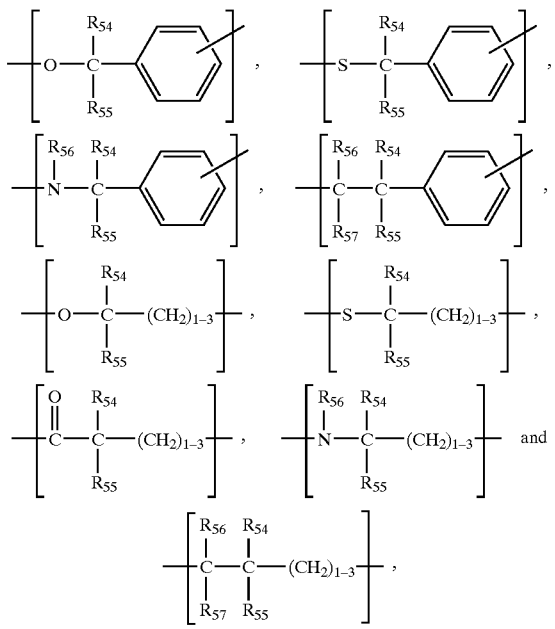

wherein $R_{54}$, $R_{55}$, $R_{56}$ and $R_{57}$ are each independently hydrogen, $C_1$–$C_8$ alkyl, $C_1$–$C_8$ haloalkyl, aryl, $C_1$–$C_8$ alkoxy, or halo. Preferred (acidic group) for $R_5$ is selected from the group consisting of —CO$_2$H, —SO$_3$H and —P(O)(OH)$_2$.

Another preferred subclass of compounds of formula (I) are those wherein $R_5$ is a non-interfering substituent, and the non-interfering substituent is independently selected from methyl, ethyl, propyl, isopropyl, thiomethyl, —O-methyl, $C_4$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —($CH_2$)$_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and carbonyl; where n is from 1 to 8.

Most preferred as non-interfering substituents are methyl, ethyl, propyl, and isopropyl.

Preferred compounds of the invention are those having the general formula (II), or a pharmaceutically acceptable salt, solvate or prodrug derivative thereof;

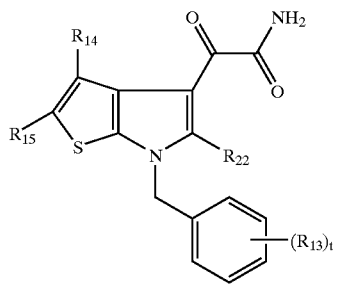

(II)

wherein;

R$_{22}$ is selected from hydrogen, methyl, ethyl, propyl, isopropyl, cyclopropyl, —F, —CF$_3$, —Cl, —Br, or —O—CH$_3$; wherein R$_{14}$ is selected from the group consisting of H, (C$_1$–C$_6$)alkyl, (C$_1$–C$_6$)alkoxy, heteroaryl, aryl, —(L$_c$)— (acylamino acid group), —(L$_h$)—(N-hydroxyfunctional amide group) or —(L$_a$)—(acidic group).

R$_{15}$ is selected from hydrogen, C$_1$–C$_8$ alkyl, C$_1$–C$_8$ alkoxy, C$_1$–C$_8$ alkylthio, C$_1$–C$_8$ haloalkyl, C$_1$–C$_8$ hydroxyalkyl, and halo.

R$_{13}$ is selected from hydrogen and C$_1$–C$_8$ alkyl, C$_1$–C$_8$ alkoxy, —S—(C$_1$–C$_8$ alkyl), C$_1$–C$_8$ haloalkyl, C$_1$–C$_8$, phenyl, halophenyl, hydroxyalkyl, and halo, and t is an integer from 0 to 5.

Also preferred are substituted pyrrole-3-oxime amide compounds of the invention represented by compounds of formula (I) or a pharmaceutically acceptable salt, solvate or prodrug derivative thereof;

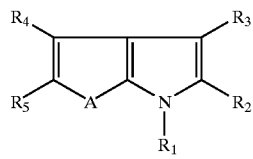

wherein;

A is O, S, or NR, and R is as described previously;

R$_1$, R$_2$, and R$_5$ are as described previously, and

R$_3$ is represented by the group —(L$_3$)— Z, where —(L$_3$)— is a divalent linker group selected from a bond or a divalent group selected from:

and Z is selected from an oxime amide or oxime thioamide group represented by the formulae,

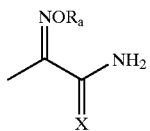

wherein, X is oxygen or sulfur; and R$_a$ is selected from hydrogen, C$_1$–C$_8$ alkyl, aryl, C$_1$–C$_8$ alkaryl, C$_1$–C$_8$ alkoxy, aralkyl and —CN;

R$_4$ is selected from the group consisting of H, (C$_1$–C$_6$) alkyl, (C$_1$–C$_6$)alkoxy, heteroaryl, aryl, —(L$_c$)— (acylamino acid group), —(Lh)—(N-hydroxyfunctional amide group) or —(L$_a$)—(acidic group).

Also preferred are substituted pyrrole-3-amide compounds of the invention represented by compounds of formula (I) or a pharmaceutically acceptable salt, solvate or prodrug thereof;

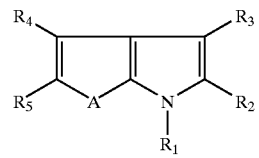

wherein;

A is O, S, or NR, and R is as described previously;

R$_1$, R$_2$, and R$_5$ are as described previously, and

R$_3$ is represented by the group —(L$_3$)—Z, where —(L$_3$)— is a divalent linker group selected from a bond or a divalent group selected from:

and Z is selected from an amide or a thioamide group represented by the formulae,

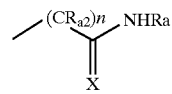

wherein, X is oxygen or sulfur; and R$_a$ is selected from hydrogen, C$_1$–C$_8$ alkyl, aryl, C$_1$–C$_8$ alkaryl, C$_1$–C$_8$ alkoxy, aralkyl and —CN; and n is 0, 1, 2 or 3;

R$_4$ is selected from the group consisting of H, (C$_1$–C$_6$) alkyl, (C$_1$–C$_6$)alkoxy, heteroaryl, aryl, —(L$_c$)— (acylamino acid group), —(L$_h$)—(N-hydroxyfunctional amide group) or —(L$_a$)—(acidic group).

21. Preferred specific compounds (and all pharmaceutically acceptable salts, solvates and prodrug derivatives thereof) which are illustrative of the compounds of the invention include compounds represented by the formulae (C1), (C2), (C3), (C4), (C5), (C6), (C7), (C8), (C9), (C10), (C11), (C12), and (C13);

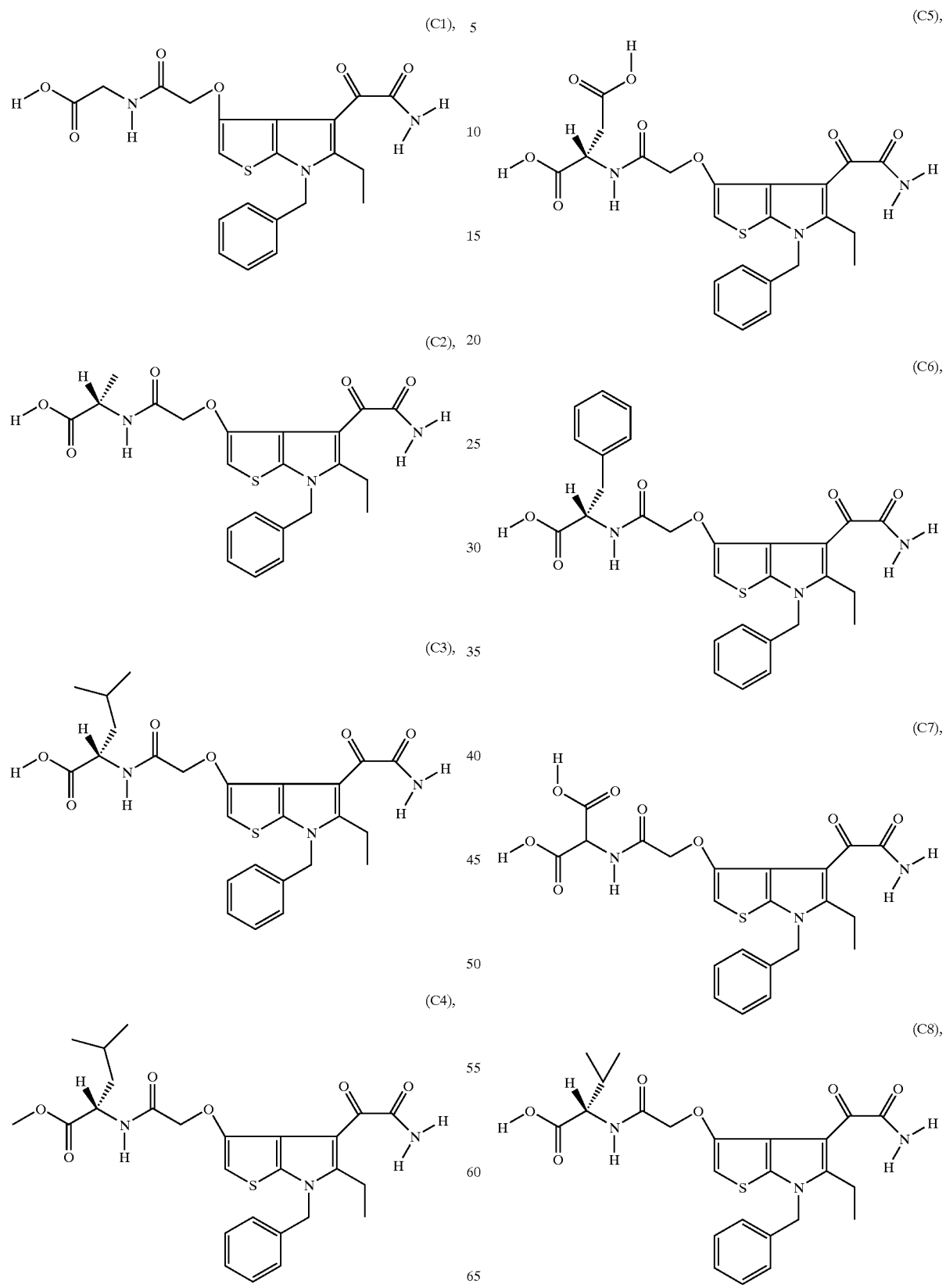

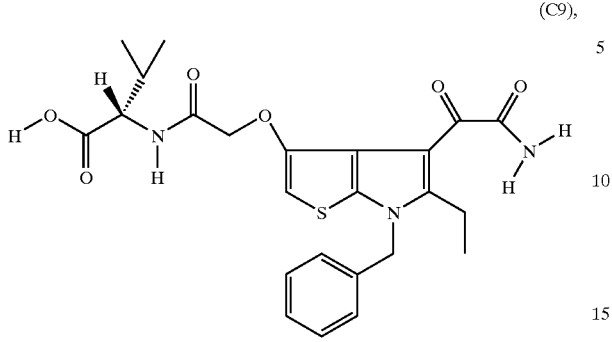

(C9),

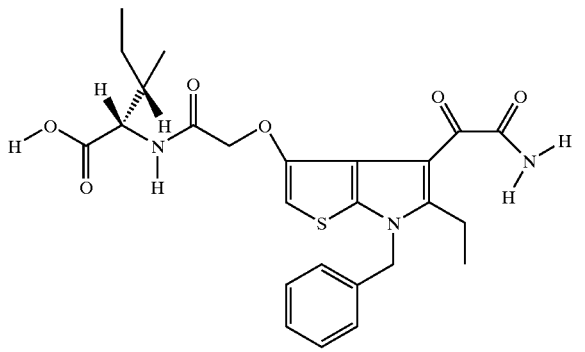

(C10),

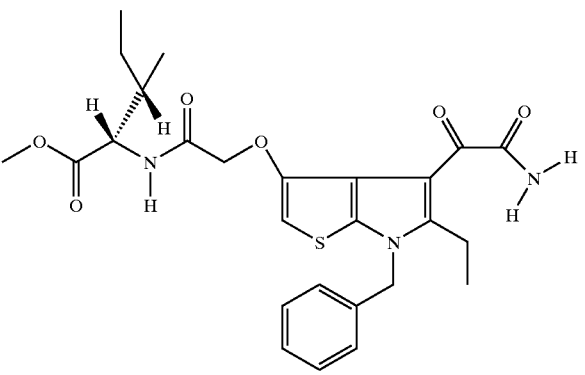

(C11),

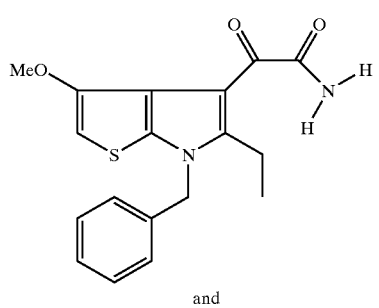

(C12), and (C13)

or a pharmaceutically acceptable salt or prodrug derivative thereof.

The salts of the above substituted pyrrole compounds represented by formulae (I) and (II) are an additional aspect of the invention. In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide; methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of diastereomers and diastereomers, because they have different melting points, different boiling points, and different solubilities can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the soduium salt of a compound of Formula (I) (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula (I) (in a medium such as dimethylformamide) 4-(2-chloroethyl) morpholine hydrochloride (available from Aldrich Chemical Co., Milwaukee, Wis. USA, Item No. C4, 220-3).

a) The substituted pyrrole-3-glyoxylamide derivative compounds of the invention are generally prepared by appending the glyoxylamide group to the 3 position of the substituted pyrrole nucleus (prepared as described infra), generating intermediates which are themselves compounds of the invention. Alternatively, this is followed by coupling the "acidic group" or the "acylamino acid group" or the "N-hydroxyfunctional amide group" at the 4 or 5 position depending on the starting material, to the intermediate above to form other compounds of the invention. Preparation of the 3-glyoxylamide intermediates 7 or 7a is as shown in scheme 1:

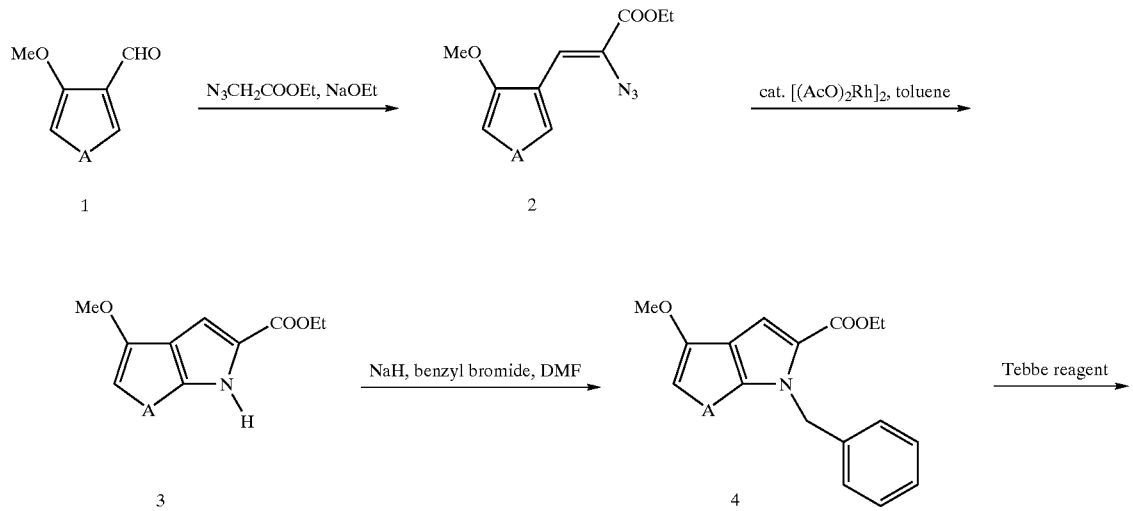

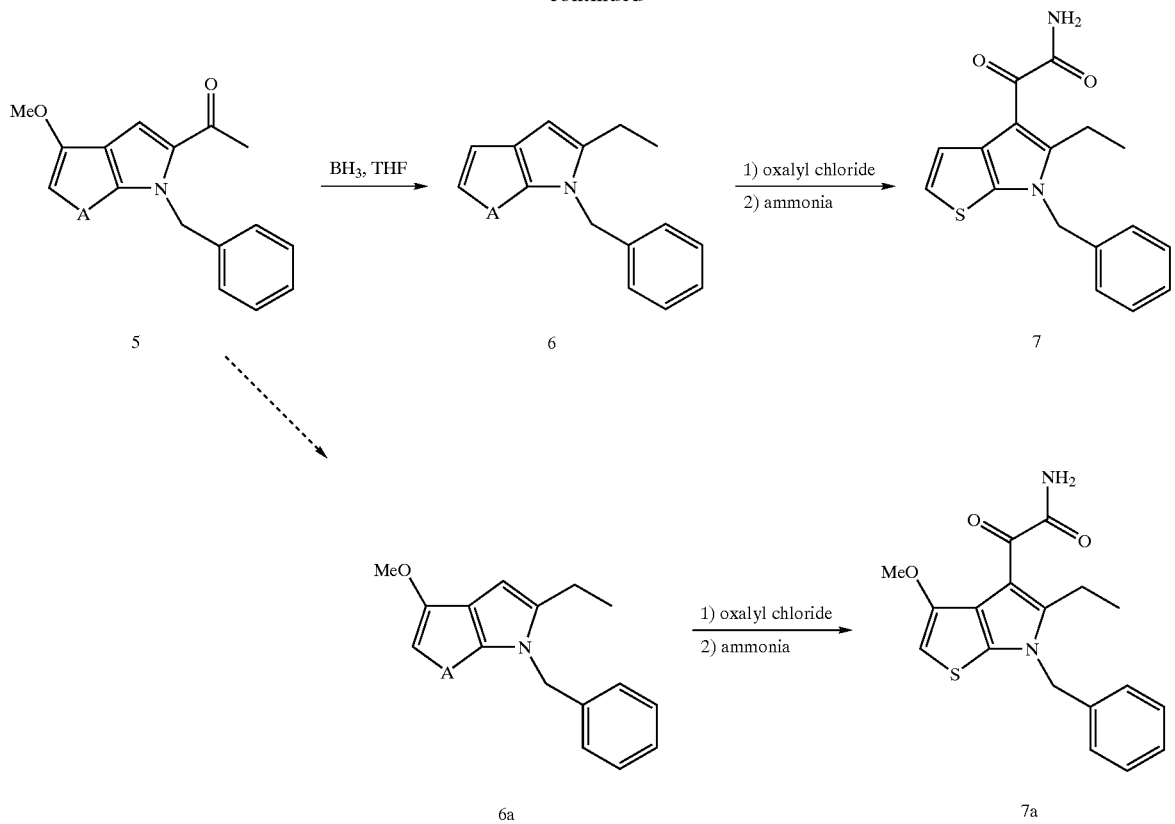

In general, a compound of formula 1 (scheme 1) wherein A is O, NR, SO, SO₂, or S is reacted with ethyl azidoacetate. In formula 1 when A is sulfur, the compound 1 is 4-methoxythiophen-3-carbaldehyde (CAS #82069-74-7) and can be synthesized in two steps from the corresponding 4-methoxythiophen-3-carboxylic acid methylester (purchased from Maybridge Chemical Company) using lithiumaluminum hydride reduction to the alcohol, followed by oxidation with for example, TPAP (tetra-n-propylammonium perruthenate(VI)) (CAS#114615-86-9, Aldrich Chemical Co., Milwaukee, U.S.A.) in combination with 4-methylmorpohline-N-oxide in methylene chloride. The use of molecular is sieves in the oxidation of alcohol to aldehyde as above is optional but preferred. The resulting starting material compound (1) is isolated by methods known to one of skill in the art, including but not limited to chromatography, crystallization, or distillation. Other compounds of formula 1 wherein A is NR, SO, or SO₂, may be purchased where available or made by methods known to one of skill in the art. The reaction to form compound (2) is catalyzed by a base, preferably a strong base such as sodium ethoxide purchased or generated as needed by dissolving sodium metal in absolute ethanol. The reagents are added at about −20° C. and allowed to warm up to about 30–50° C. over 30 to 60 minutes. The reaction mixture is worked-up by dilution with water and filtration, or by aqueous extraction as necessary to afford the azidoacrylate compound of formula (2). The compound of formula (2) is ring closed to afford the compound of formula (3) under heating, and preferably in the presence of a catalyst. The preferred reaction conditions include heating compound (2) in refluxing toluene or other suitable solvent in the presence of a catalytic amount of a catalyst, e.g. rhodium acetate dimer.

The product substituted pyrrole compound (3) is isolated by concentration followed by recrystallization. Other methods of isolation are within the purview of this invention and are known to one of skill in the art. The compound of formula (3) is transformed to the compound of formula (4) or analog thereof, by reacting compound (3) with an organic halide in the presence of a base such as for example sodium hydride and in the presence of a solvent such for example dimethylformamide. For example, treatment of compound (3) with sodium hydride in DMF followed by addition of benzylbromide results in compound (4) upon work-up. The compound of formula (4) is converted to the ketone, for example, the methylketone. Preparation of compound (5) is accomplished for example, by reaction of compound (4) with µ-chloro-µ-methylenelbis(cyclopentadienyl)-titanium) dimethylaluminum (Tebbe reagent). The formation of the methylketone derivative using the Tebbe reagent involves addition of about 1.2 molar equivalent of Tebbe reagent to a cold (about 0° C.) solution of compound (4) in tetrahydrofuran followed by warming to about room temperature. Upon satisfactory completion of the reaction as determined by common laboratory methods, i.e., HPLC, GC, TLC, GCMS etc, the reaction fixture is quenched by addition of saturated aqueous potassium carbonate. This likely results in vigorous evolution of gas. The product (5) is isolated upon aqueous extractive work up procedures and standard purification methods, i.e. chromatography and/or crystallization.

The compound of formula (5) may be converted to the compound of formula (6) or (6a). The compound of formula (6) may be obtained for example, by use of borane.tetrahydrofuran complex (CAS#14044-65-6, Aldrich Chemical Co.) or other method suitable for the reduction of compound (5) in THF or other suitable solvent or solvent mixture. The compound of formula (6a) may be obtained by the use of mild and/or selective reducing agents and/or reaction conditions which do not affect the methoxy substituent at position 4 or 5 depending on the starting material employed. The compound of formula (6) or (6a) may be reacted with oxalyl chloride followed by reaction with ammonia (THF solution saturated with ammonia) to afford the compound of formula (7) or the corresponding analog compound of formula (7a).

Conversion of the 3-glyoxylamide intermediate to the acidic group derivatives at position 4 or 5 is shown for example in scheme 1A below:

Compounds (7), (7a), (8a), (9a) and (10a) are also compounds contemplated to be within the scope of the present invention.

Functionalization of position 4 or 5 of compound (10a) to the acylamino acid derivative (10c) may be accomplished by room temperature base catalyzed condensation of the amino acid protected at the acid terminus (using a protecting group known in the literature but preferably the methyl ester), with the substituted pyrrole-3-glyoxylamide acid derivative compound of formula (10a) for example. The reaction is accomplished using coupling agents such as HOBT/EDCI, BOP/collidine or other amide bond forming coupling agents.

Scheme 1A

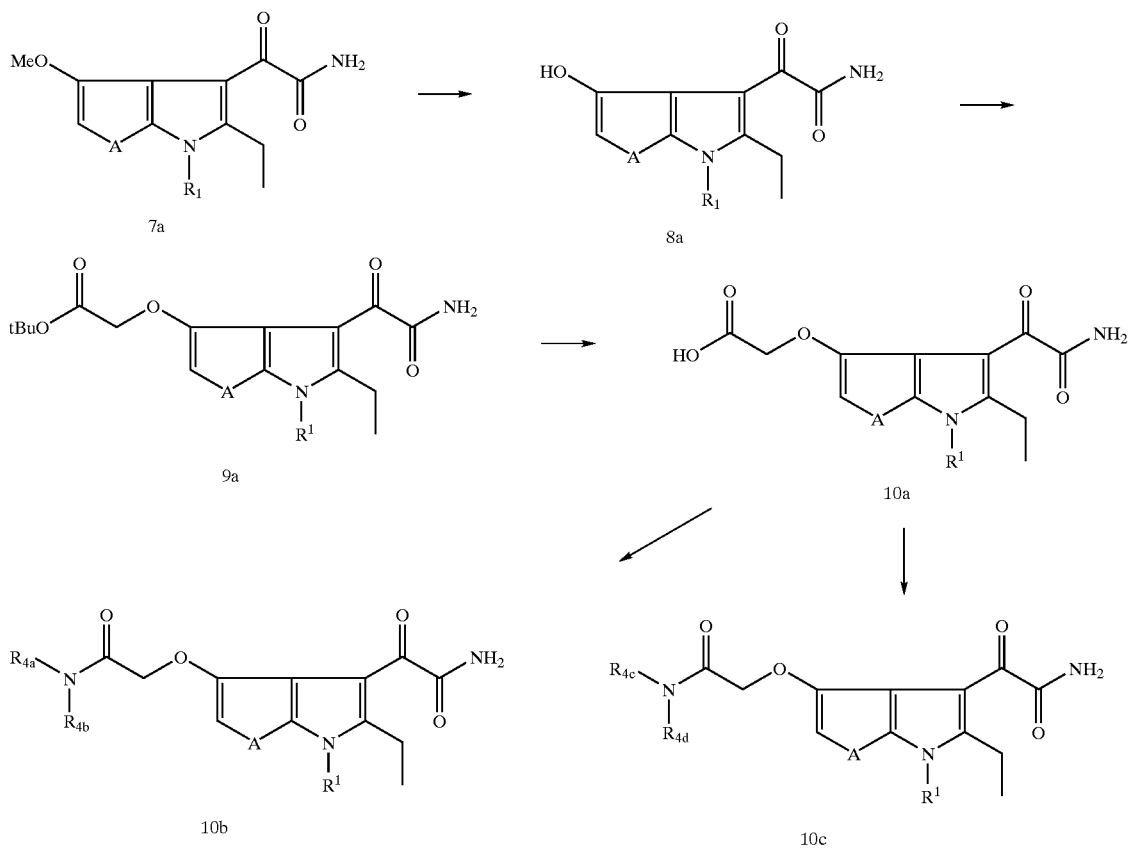

According to scheme 1A, the compound of formula (7a) may be demethylated for example with boron tribromide in methylene chloride or other suitable solvent to afford the compound of formula (8a). The compound of formula (8a) may be o-acylated, o-alkylated, o-arylated or otherwise converted to a compound represented within the scope of $R_4$. For example reaction of compound (8a) with NaH/mineral oil and a α-bromoalkanoic acid ester e.g. α-bromoethylacetate affords the compound of formula (9a). The compound of formula (9a) may be converted to the free acid (boa) by hydrolysis. The free acid (10a) may in turn be converted to the acid salt or to derivatives such as the ester or amide by procedures known to one of skill in the art or found in general reference texts (J. March *Advanced Organic Chemistry*, Wiley Interscience publishers, New York, N.Y., 1985, and R. C. Larock *Comprehensive Organic Transformations*, VCH Publishers, New York, N.Y., 1989).

Similarly, the N-hydroxyfunctional amide group may be introduced via the acid (10a) or acid salt thereof, by reaction with for example hydroxylamine hydrochloride or substituted hydroxylamine hydrochloride to afford the N-hydroxyfunctional amide compound of formula (10b).

b) Substituted pyrrole-3-acetamide derivative sPLA$_2$ inhibitors.

Substituted pyrrole-3-acetamide sPLA$_2$ inhibitor derivatives of compounds (6) or (6a) may be lithiated at the (3) position with an organolithium reagent e.g. n-butyllithium, followed by quenching the lithiated intermediate with ethylene oxide for example, to afford upon hydrolysis, the terminal alcohol derivative (10d) at position (3) (scheme 2):

Scheme 2

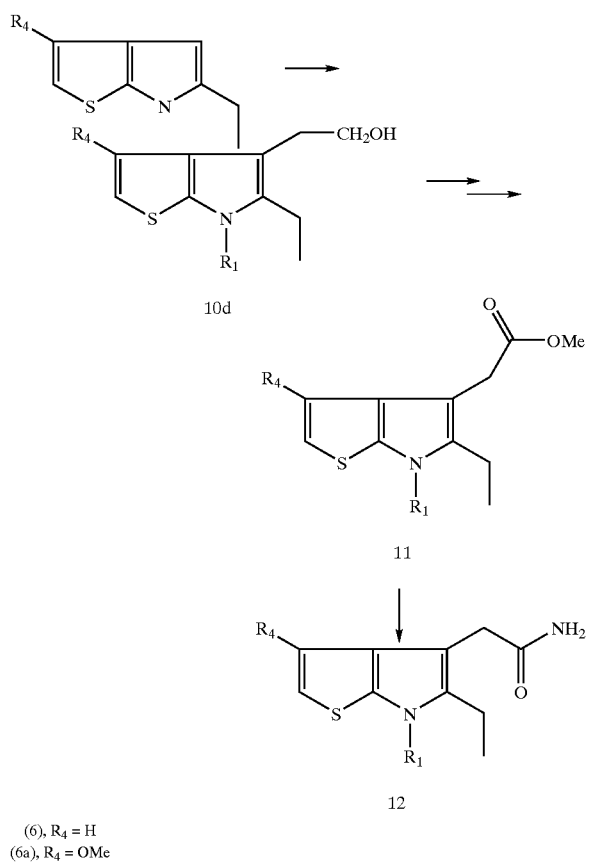

(6), R₄ = H
(6a), R₄ = OMe

The resulting alcohol intermediate (10d), itself a compound of the invention may be converted by oxidation to the acid and further converted to the ester (11). Conversion of the alcohol intermediate (10d) to compound ester via an intermediate acid may be accomplished by oxidation of the alcohol with sodium hypochlorite in buffered t-butanol for example, followed by esterification of the incipient acid to the ester (11). Methods for these conversions are known to one of skill in the art and may be found in general reference texts disclosed herein. The ester (11) may be converted to the acetamide derivative (12) or other substituted acetamide compound. For example the reaction of the acetate (11) with methylchloroaluminum amide in benzene or other suitable solvent or solvent mixtures affords the acetamide (compound 12). (See Levin, J. I.; Turos, E.; Weinreb, S. M. *An alternative procedure for the aluminum-mediated conversion of esters to amides. Syn.Comm.*, 1982, 12, 989–993).

Similarly, use of N-substituted methylchloroaluminum amides result in the corresponding substituted acetamides (see Weinreb supra). The 3-substituted amide or acetamide substituted pyrrole compounds described above may be converted to the corresponding 4-substituted acylamino acid compounds or the 4-substituted N-hydroxyfunctional amide compounds as described previously for the glyoxylamide compounds.

c) The substituted pyrrole-3-oxime amide compounds of the invention can be prepared following protocol of scheme 3 below:

Scheme 3

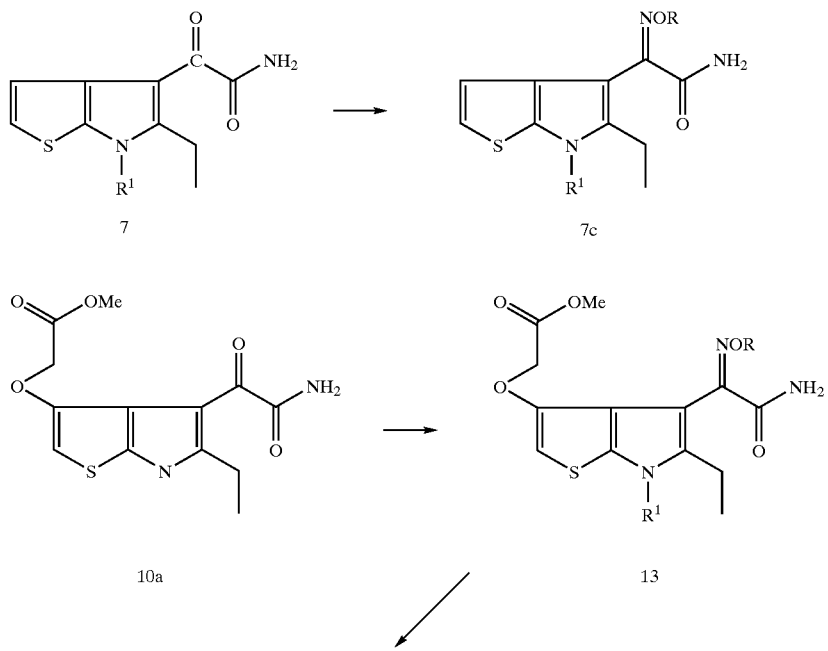

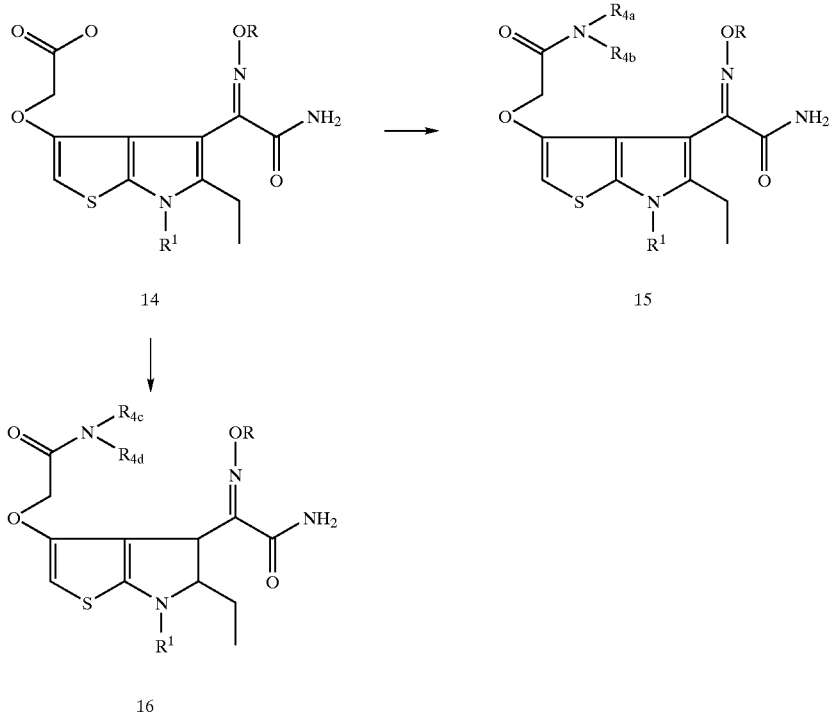

To introduce the oxime functionality, the compound of formula (7), for example, is heated with hydroxylamine hydrochloride (when R is H) in a THF/methanol mixture for about 1 to 8 hours or until the reaction is deemed complete. The reaction product compound (7c), a compound of the invention, is isolated by chromatography or other known laboratory procedure. Substituted oximes such as when R is methyl, ethyl, phenyl or other non-interfering substituent may be prepared by reaction of the corresponding substituted hydroxylamine hydrochloride or free base with the glyoxylamide (e.g. compound 7) as described supra.

Similarly, the ester i.e. methylester of the acid compound (10a), or the acid salts thereof, may be converted to the corresponding oxime or substituted oxime functionality at position (3) by the method described above. The ester functionality at the (4) or (5) position on the substituted pyrrole nucleus, as in for example, compound (13), may be converted to the acid by hydrolysis using lithium hydroxide or other known ester hydrolysis methods to afford a compound of formula (14). See, for example, J. March *Advanced Organic Chemistry*, Wiley Interscience publishers, New York, N.Y., 1985, and R. C. Larock *Comprehensive Organic Transformations*, VCH Publishers, New York, N.Y., 1989.

Furthermore, the oxime compounds prepared as described above may be converted to the N-hydroxyfunctional amide at the 4 or 5 position, via the free acid, the ester or the acid salt functionalities at the 4 or 5 position. For example, scheme 3 shows the conversion of the free acid compound (14) to the N-hydroxyfunctional amide compound (15).

Likewise, the compound (14) and analogs thereof may be converted to the acylamino acid compound (16) and corresponding homologs thereof by procedures described supra.

IV. Methods of Using the Compounds of the Invention

The substituted pyrrole compounds described herein are believed to achieve their beneficial therapeutic action principally by direct inhibition of mammalian (including human) sPLA$_2$, and not by acting as antagonists for arachidonic acid, nor other active agents below arachidonic acid in the arachidonic acid cascade, such as 5-lipoxygenases, cyclooxygenases, and etc.

The method of the invention for inhibiting sPLA$_2$ mediated release of fatty acids comprises contacting mammalian sPLA$_2$ with a therapeutically effective amount of substituted pyrrole compounds corresponding to formulae (I) or (II) as described herein including salt or a prodrug derivative thereof.

Another aspect of this invention is a method for treating Inflammatory Diseases such as inflammatory bowel disease, septic shock, adult respiratory distress syndrome, pancreatitis, trauma, bronchial asthma, allergic rhinitis, rheumatoid arthritis, osteoarthritis, and related diseases which comprises administering to a mammal (including a human) a therapeutically effective dose of the substituted pyrrole compound of the invention (see, formulae I and II).

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of bodyweight of an active compound of this invention.

Preferably compounds of the invention (per Formula I or II) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the substituted pyrrole compound of the invention together with a pharmaceutically acceptable carrier or diluent therefor. The present pharmaceutical formulations are prepared by known procedures using well known and readily available ingredients.

In making the compositions of the present invention, the Active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable-carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In tablets the Active ingredient is mixed with a carrier having the necessary binding properties in suitable proportions and compacted in the shape and size desired. The powders and tablets preferably contain from about 1 to about 99 weight percent of the Active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active ingredient can be dissolved or suspended in a pharmaceutically acceptable carrier, such as sterile water, sterile organic solvent or a mixture of both. The Active ingredient can often be dissolved in a suitable organic solvent, for instance aqueous propylene glycol. Other compositions can be made by dispersing the finely divided Active ingredient in aqueous starch or sodium carboxymethyl cellulose solution or in a suitable oil.

The following pharmaceutical formulations 1 thru 8 are illustrative only and are not intended to limit the scope of the invention in any way. "Active ingredient", refers to a compound according to Formula (I) or (II) or a pharmaceutically acceptable salt, solvate, or prodrug thereof.

FORMULATION 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

FORMULATION 2

A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

FORMULATION 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of Active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |

FORMULATION 4-continued

Tablets, each containing 60 mg of Active ingredient, are made as follows:

| | |
|---|---|
| Sodium carboxymethyl starch | 4.5 mg |
| Magnesium stearate | 0.5 mg |
| Talc | 1 mg |
| Total | 150 mg |

The Active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of Active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The Active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of Active ingredient, are made as follows:

| | |
|---|---|
| Active ingredient | 225 mg |
| Saturated fatty acid glycerides | 2,000 mg |
| Total | 2,225 mg |

The Active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of Active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| | |
|---|---|
| Active ingredient | 100 mg |
| Isotonic saline | 1,000 ml |

The solution of the above ingredients generally is administered intravenously to a subject at a rate of 1 ml per minute.

All of the products of the Examples described below as well as intermediates used in the following procedures showed satisfactory NMR and IR spectra. They also had the correct mass spectral values.

To a suspension of lithium aluminum hydride (5.19 g, 137 mmol) in tetrahydrofuran (75 mL) cooled to 0° C. was added a solution of 4-methoxythiophene-3-carboxylic acid methyl ester (23.5 g, 137 mmol) in tetrahydrofuran (125 mL) over 15 min. The resulting mixture was stirred at room temperature for 1 h. The solvent volume was doubled with hexane and the resulting mixture treated carefully with 5 N sodium hydroxide solution (10 mL). The resulting mixture was stirred at room temperature for 2 h then filtered. The solids were washed thoroughly with fresh portions of diethyl ether. The combined organic filtrates were dried (sodium sulfate), filtered, and concentrated in vacuo to provide 18.2 g (93%) of the title compound as a pale yellow oil. $^1$H NMR (CDCl$_3$) δ 7.11 (d, J=2 Hz, 1H), 6.23 (d, J=2 Hz, 1H), 4.58 (s, 2H), 3.85 (s, 3H), 2.09 (s, 1H); MS ES+m/e 145 (p+1); IR (CHCl$_3$, cm$^{-1}$) 3603, 3012, 1565, 1478.

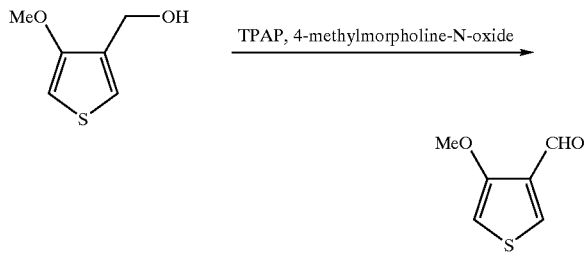

A solution of (4-methoxythiophen-3-yl)methanol (0.370 g, 2.57 mmol) and 4-methylmorpholin-N-oxide (0.328 g, 2.83 mmol) in methylene chloride (5 mL) was treated with tetrapropylammonium perruthenate (5 mg) at room temperature for 2 h Additional portions of 4-methylmorpholin-N-oxide (100 mg) and tetrapropylammonium perruthenate (5 mg) were added and the resulting mixture stirred for 18 h. The. mixture was filtered down a short column of silica gel, which was washed thoroughly with diethyl ether. The combined filtrates were concentrated in vacuo to provide 0.31 g (85%) of the title product as a yellow oil. $^1$H NMR (CDCl$_3$) δ 9.86 (s, 1H), 8.00 (d, J=2 Hz, 1H), 6.25 (d, J=2 Hz, 1H), 3.89 (s, 3H).

EXAMPLE 1

2-(6-Benzyl-5-ethyl-6H-thieno[2,3-b]pyrrol-4-yl)-2-oxoacetamide

A. Preparation of 2-Azido-3-(4-methoxythiophen-3-yl)acrylic Acid Ethyl Ester

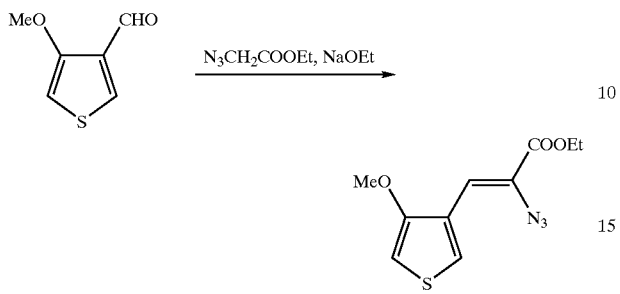

Sodium (20.0 g, 0.870 mol) was dissolved in absolute ethanol (550 mL) and the resulting solution cooled to −15° C. A mixture of 4-methoxy-3-thiophenaldehyde (32.4 g, 0.228 mol) and ethyl azidoacetate (118 g, 0.914 mol) in absolute ethanol (30 mL) and ether (30 mL) was added slowly such that the temperature of the reaction mixture did not rise above −10° C. The mixture warmed to −40° C. over 40 min accompanied by vigorous gas evolution. After 3 h the mixture was diluted with water (1 L) and the resulting precipitate was collected via vacuum filtration to provide 31.8 g (55%) of the title compound. Recrystallization (hexanes) of an analytical sample provided yellow crystals: mp 88–90° C. $^1$H NMR (CDCl$_3$) 88.14 (d, J=3.3 Hz, 1H), 6.94 (s, 1H), 6.19 (d, J=3.3 Hz, 1H), 4.35 (q, J=7.0 Hz, 2H), 3.86 (s, 3H), 1.41 (t, J=7.0 Hz, 3H); MS ES+m/e 254 (p+1); IR (KBr, cm$^{-1}$) 2114, 1700, 1256. Anal. Calcd for $C_{10}H_{11}N_3O_3S$: C, 47.42; H, 4.38; N, 16.59. Found: C, 47.09; H, 4.46; N, 15.87.

B. Preparation of 3-Methoxy-6H-thieno[2,3-b]pyrrole-5-carboxylic Acid Ethyl Ester.

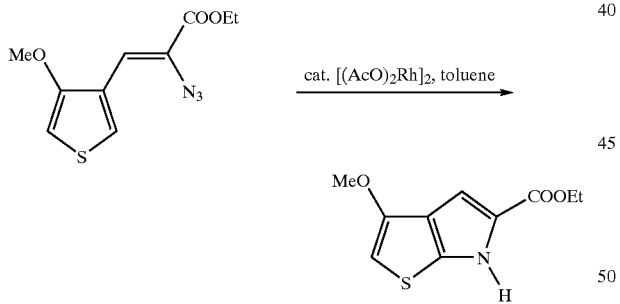

A mixture of 2-azido-3-(4-methoxythiophen-3-yl)acrylic acid ethyl ester (11.0 g, 43.3 mmol) and rhodium acetate dimer (330 mg, 0.75 mmol) in toluene (300 mL) was heated at reflux for 1.5 h. The mixture was cooled to room temperature and filtered through a short pad of silica gel. The filtrate was concentrated in vacuo to provide 8.8 g (90%) of the title compound as a pale yellow solid. Recrystalization (ethyl acetate/hexanes) provided an analytical sample: mp 119–121° C. $^1$H NMR (CDCl$_3$) δ 9.73 (bs, 1H), 7.07 (d, J=1.8 Hz, 1H), 5.76 (s, 1H), 4.38 (q, J=7.0 Hz, 2H), 3.88 (s, 3H), 1.38 (t, J=7.0 Hz, 3H); $^{13}$C NMR (CDCl$_3$) δ 161.55, 149.21, 135.93, 127.92, 124.28, 106.44, 90.40, 60.74, 57.09, 14.41; MS ES+m/e 226 (p+1); IR (CHCl$_3$, cm$^{-1}$) 3480, 1692, 1511, 1278. Anal. Calcd for $C_{10}H_{11}NO_3S$: C, 53.32; E, 4.92; N, 6.22. Found: C, 53.26; H, 4.91; N, 6.16.

C. Preparation of 6-Benzyl-3-methoxy-6H-thieno[2,3-b]pyrrole-5-carboxylic Acid Ethyl Ester.

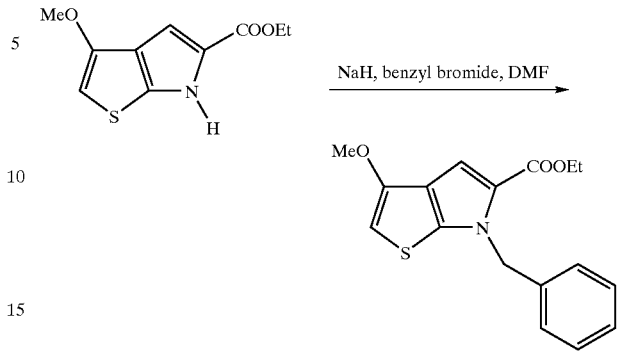

A solution of 3-methoxy-6H-thieno[2,3-b]pyrrole-5-carboxylic acid ethyl ester (8.08 g, 35.9 mmol) in N,N-dimethylformamide (150 mL) was treated with sodium hydride as a 60% dispersion in mineral oil (1.90 g, 47.5 mmol) that had been washed with hexanes. After stirring for 30 min, benzyl bromide (5.1 mL, 43 mmol) was added and the resulting mixture stirred for 96 h. The mixture was diluted with water and the resulting mixture extracted three times with ethyl acetate. The combined organic extracts were washed once with water, once with saturated sodium chloride solution, dried (sodium sulfate), filtered, and concentrated in vacuo to provide 11.0 g (97%) of the title compound. Recrystallization (absolute ethanol) provided an analytical sample as off-white needles: mp 77–79° C. $^1$H NMR (CDCl$_3$) δ 7.15–7.40 (m, 6H), 5.75 (s, 1H), 5.64 (s, 2H), 4.30 (q, J=7.0 Hz, 2H), 3.89 (s, 3H), 1.35 (t, J=7.0 Hz, 3H); MS ES+m/e 316 (p+1); IR (CHCl$_3$, cm$^{-1}$) 1696, 1534, 1274. Anal. Calcd for $C_{17}H_{17}NO_3S$: C, 64.74; H, 5.43; N. 4.44. Found: C, 64.69; H, 5.48; N, 4.87.

D. Preparation of 1-(6-Benzyl-3-methoxy-6H-thieno[2,3-b]pyrrol-5-yl)ethanone.

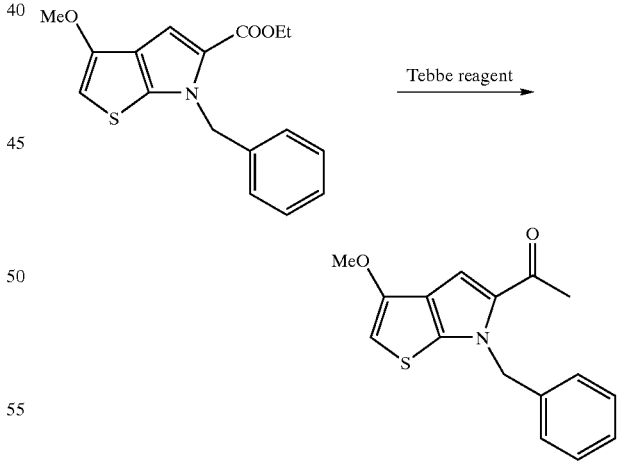

A solution of 6-benzyl-3-methoxy-6H-thieno[2,3-b]pyrrole-5-carboxylic acid ethyl ester (5.00 g, 15.9 mmol) in tetrahydrofuran (75 mL) was cooled to 0° C. and treated with 0.5 M Tebbe reagent in toluene (38 mL). The mixture was warmed to room temperature and stirred for 3 h. A solution of saturated aqueous potassium carbonate (140 mL) was added carefully resulting in vigorous gas evolution. The mixture was extracted twice with ethyl acetate. The combined organic layers were washed once with water, once with saturated sodium chloride solution, dried (sodium sulfate), filtered, and concentrated in vacuo. Chromatography (silica gel, 10% ethyl acetate/90% hexanes) provided 1.50 g (33%) of the title compound as a yellow oil that solidified upon cooling to −10° C. Recrystallization (hexanes) provided an analytical sample as a beige solid: mp 90–92° C. $^1$H NMR (CDCl$_3$) δ 7.30 (m, 5H), 7.19 (s, 1H), 5.77 (s, 1H), 5.68 (s, 2H), 3.90 (s, 3H), 2.51 (s, 3H); MS ES+m/e 286 (p+1); IR (KBr, cm$^{-1}$) 3436, 1656, 1530, 1277. Anal. Calcd for C$_{16}$H$_{15}$NO$_2$S: C, 67.34; H, 5.30; N, 4.91. Found: C, 67.72; H, 5.33; N, 5.03.

E. Preparation of 6-Benzyl-5-Ethyl-6H-Thieno[2,3-b]Pyrrole.

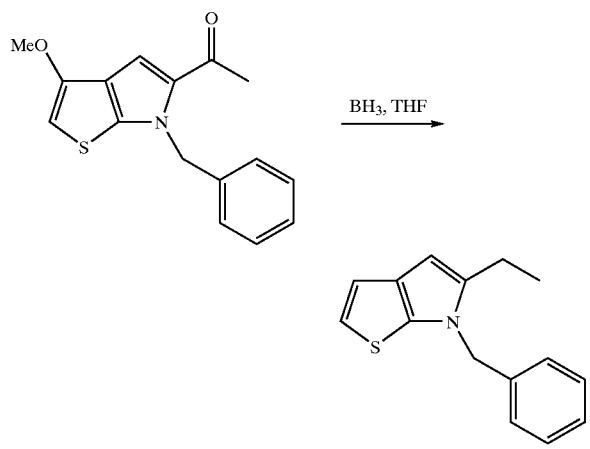

A solution of 1-(6-benzyl-3-methoxy-6H-thieno[2,3-b]pyrrol-5-yl)ethanone (900 mg, 3.15 mmol) in tetrahydrofuran (10 mL) was treated with 1 M borane in tetrahydrofuran (10 mL, 10 mmol) at room temperature for 64 h. Excess acetone was added and the resulting mixture refluxed for 1 h (hour) and stirred for 18 h at room temperature. The mixture was concentrated in vacuo and the residue dissolved in ethyl acetate. The solution was washed once with water, once with aqueous saturated sodium chloride solution, dried (sodium sulfate), filtered, and concentrated in vacuo. Chromatography (silica gel, chloroform) of the residue provided 225 mg (30%) of the title compound. $^1$H NMR (DMSO-d$_6$) δ 7.30 (m, 3H), 7.12 (d, J=7.0 Hz, 2H), 6.93 (d, J=5.1 Hz, 1H), 6.86 (s, J=5.1 Hz, 1H), 6.16 (s, 1H), 5.20 (s, 2H), 2.68 (q, J=7.5 Hz, 2H), 1.21 (t, J=7.5 Hz, 3H); MS ES+m/e 242 (p+1).

F. Preparation of 2-(6-Benzyl-5-ethyl-6H-thieno[2,3-b]pyrrol-4-yl)-2-oxoacetamide.

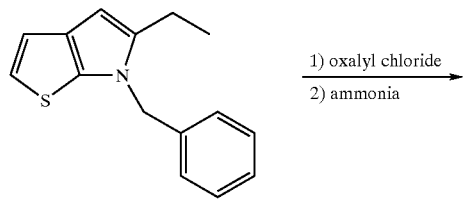

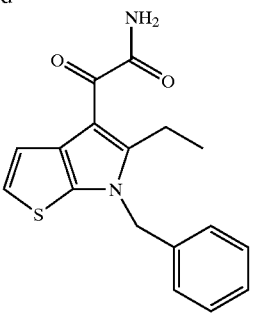

A solution of 6-benzyl-5-ethyl-6H-thieno[2,3-b]pyrrole (0.21 g, 0.88 mmol) in methylene chloride (4 mL) was cooled in an ice bath and treated with oxalyl chloride (0.40 mL, 4.6 mmol). The mixture was allowed to warm to room temperature over 1.5 h, concentrated in vacuo, dissolved in chloroform, and concentrated in vacuo. The residue was dissolved in methylene chloride and treated with 0.5 M ammonia in dioxane (5 mL). The resulting mixture was stirred for 1 h and concentrated in vacuo. Chromatography (silica gel, 40% ethyl acetate/60% hexanes) of the residue provided 32 mg of a solid that was slurried in ethyl acetate/hexanes and filtered to give 10 mg (4%) of the title compound as a yellow solid: mp 169–172° C. $^1$H NMR (CDCl$_3$) δ 7.44 (d, J=5.1 Hz, 1H), 7.32 (m, 3H), 7.15 (m, 2H), 6.94 (bs, 1H), 6.88 (d, J=5.5 Hz, 1H), 5.47 (bs, 1H), 5.21 (s, 2H), 3.11 (q, J=7.3 Hz, 2H), 1.18 (t, J=7.3 Hz, 3H). TOF MS ES$^+$ exact mass calculated for C$_{17}$H$_{17}$N$_2$O$_2$S (p+1): m/z= 313.1010. Found: 313.1018.

Assay

The following chromogenic assay procedure was used to identify and evaluate inhibitors of recombinant human secreted phospholipase A$_2$. The assay described herein has been adapted for high volume screening using 96 well microtiter plates. A general description of this assay method is found in the article, "Analysis of Human Synovial Fluid Phospholipase A$_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents:

| REACTION BUFFER - | |
|---|---|
| CaCl$_2$.2H$_2$O | (1.47 g/L) |
| KCl | (7.455 g/L) |
| Bovine Serum Albumin (fatty acid free) (Sigma A-7030, product of Sigma Chemical Co., St Louis MO, USA) | (1 g/L) |
| TRIS HCl | (3.94 g/L) |
| pH 7.5 | (adjust with NaOH) |

ENZYME BUFFER—
  0.05 NaOAc.3H$_2$O, pH 4.5
  0.2 NaCl
  Adjust pH to 4.5 with acetic acid
  DTNB—5,5'-dithiobis-2-nitrobenzoic acid
RACEMIC DIHEPTANOYL THIO—PC
  racemic 1,2-bis(heptanoylthio)-1,2-dideoxy-sn-glycero-3-phosphorylcholine TRITON X-100™ prepare at 6.249 mg/ml in reaction buffer to equal 10 μM.

REACTION MIXTURE—

A measured volume of racemic diheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:

1. Add 0.2 mL reaction mixture to all wells;
2. Add 10 uL test compound (or solvent blank) to appropriate wells, mix 20 seconds;
3. Add 50 nanograms of sPLA$_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, IC$_{50}$ values were determined. Typically, the IC$_{50}$ values (see; Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of IC$_{50}$ values. IC$_{50}$ values were determined by plotting log concentration versus inhibition values in the range from 10–90% inhibition.

Results of Human Secreted Phospholipase A$_2$ Inhibition Test

TABLE 1

| Compound | Inhibition of human secreted PLA$_2$ IC50 ± mean deviation (3–4 tests) (uM) |
| --- | --- |
| (structure) | 5.5 |

While the present invention has been illustrated above by certain specific embodiments, it is not intended that these specific examples should limit the scope of the invention as described in the appended claims.

We claim:

1. A substituted pyrrolo compound represented by the formula (I), or a pharmaceutically acceptable salt, solvate, or prodrug derivative thereof;

(I)

wherein;

A is S, SO, SO$_2$, O, or NR, and R is a non-interfering substituent;

R$_1$ is selected from groups (a), (b), and (c) wherein;
(a) is C$_7$–C$_{20}$ alkyl, C$_7$–C$_{20}$ haloalkyl, C$_7$–C$_{20}$ alkenyl, C$_7$–C$_{20}$ alkynyl, carbocyclic radical, or heterocyclic radical, or
(b) is a member of (a) substituted with one or more independently selected non-interfering substituents; or
(c) is the group —(L$_1$)—R$_{11}$; where, —(L$_1$)— is a divalent linking group of 1 to 8 atoms and where R$_{11}$ is a group selected from (a) or (b);

R$_2$ is hydrogen, or a group containing 1 to 4 non-hydrogen atom plus any required hydrogen atoms;

R$_3$ is —(L$_3$)— Z, where —(L$_3$)— is a divalent linker group selected from a bond or a divatent group selected from;

$$-\underset{H_2}{C}-, \quad -O-, \quad -S-, \quad -\underset{H}{N}- \text{ or}$$

$$-\underset{\parallel}{\overset{\parallel}{C}}-$$
$$O$$

and Z is selected from a group represented by the formulae, wherein, X is oxygen or sulfur; and R$_a$ is selected from hydrogen, C$_1$–C$_8$ alkyl, aryl, C$_1$–C$_8$ alkaryl, C$_1$–C$_8$ alkoxy, aralkyl and —CN;

R$_4$ is the group hydrogen; or the group WR$^{4e}$ wherein W is oxygen, Sulfur or NH, and R$^{4e}$ is an alkyl, aryl or an alkylaryl group; or the group —(L$_a$)—(acidic group); wherein —(L$_a$)—, is an acid linker having an acid linker length of 1 to 8; or the group —(L$_h$)—(N-hydroxyfunctional amide group); wherein —(L$_h$)—, is an N-hydroxyfunctional amide linker having an N-hydroxyfunctional amide linker length of 1 to 8;

or the group —(L$_c$)—(acylamino acid group); wherein —(L$_c$)—, is an acylamino acid linker having an acylamino acid linker length of 1 to 8;

R$_5$ is selected from hydrogen, a non-interfering substituent, or the group, —(L$_a$)—(acidic group); wherein —(L$_a$)—, is an acid linker having an acid linker length of 1 to 8.

2. The compound of claim 1 wherein $R_2$ is hydrogen, $C_2$–$C_4$ alkyl, $C_2$–$C_4$ alkenyl, —O—($C_1$–$C_3$ alkyl), —S—($C_1$–$C_3$ alkyl), $C_3$–$C_4$ cycloalkyl, —$CF_3$, halo, —$NO_2$, —CN, or —$SO_3$.

3. The compound of claim 1 wherein the acid linker group, —($L_a$)—, for $R_4$ is a divalent group selected from,

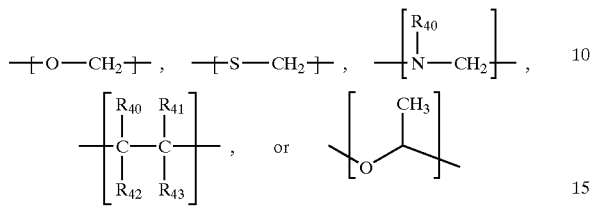

where $R_{40}$, $R_{41}$, $R_{42}$, and $R_{43}$ are each independently selected from hydrogen, $C_1$–$C_8$ alkyl.

4. The compound of claim 1 wherein $R_4$ is hydrogen.

5. The compound of claim 1 wherein $R_4$ is $WR_{4e}$, and wherein W is oxygen, and $R_{4e}$ is a group selected from hydrogen, ($C_1$–$C_4$)alkyl, and aryl.

6. The compound of claim 1 wherein R4 is the group —($L_c$)—(acylamino acid group).

7. The compound of claim 1 wherein $R_5$ is hydrogen.

8. The compound of claim 1 wherein A is sulfur.

9. The compound of claim 1 wherein for $R_3$, Z is the group represented by the formula;

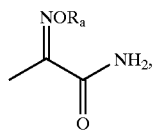

and the linking group —($L_3$)— is a bond; and $R_a$ is hydrogen, methyl, ethyl, propyl, isopropyl, phenyl or benzyl.

10. The compound of claim 1 wherein for $R_3$, Z is the group represented by the formula;

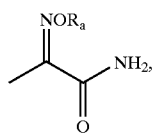

and the linking group —($L_3$)— is a bond; and $R_a$ is hydrogen.

11. The compound of claim 1 wherein for $R_3$, Z is the group represented by the formula;

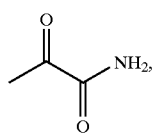

and the linking group —($L_3$)— is a bond.

12. The compound of claim 1 wherein for $R_3$, Z is the group represented by the formula;

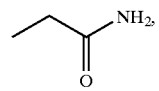

and the linking group —($L_3$)— is a bond.

13. The compound of claim 1 wherein for $R_1$ the divalent linking group —($L_1$)— is selected from a group represented by the formulae (Ia), (Ib), (Ic), (Id), (Ie), and (If):

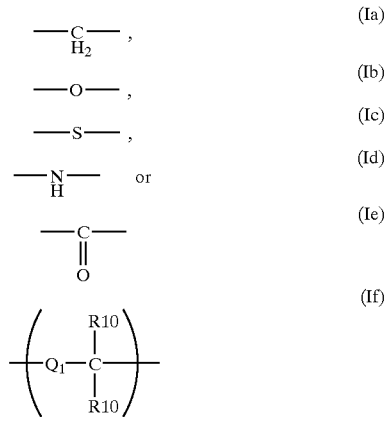

where $Q_1$ is a bond or any of the divalent groups Ia, Ib, Ic, Id, and Ie and $R_{10}$ is independently —H, $C_{1-8}$ alkyl, $C_{1-8}$ haloalkyl or $C_{1-8}$ alkoxy.

14. The compound of claim 1 wherein the linking group —($L_1$)— of $R_1$ is —($CH_2$)— or —($CH_2$—$CH_2$)—.

15. The compound of claim 1 wherein the linking group —($L_{11}$)— of $R_{11}$ is a bond and $R_{11}$ is —($CH_2$)m—$R^{12}$ wherein m is an integer from 1 to 6, and $R^{12}$ is a group represented by the formula:

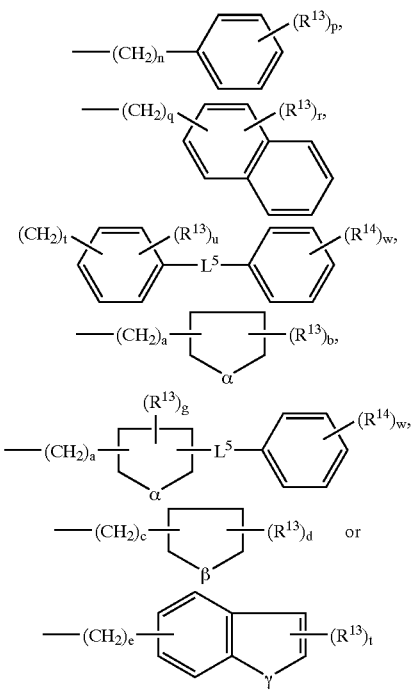

wherein a, c, e, n, q and t are independently an integer from 0 to 2, $R^{13}$ and $R^{14}$ are independently selected from a halogen, $C_1$ to $C_8$ alkyl, $C_1$ to $C_8$ alkyloxy, $C_3$ to $C_8$ alkylthio, aryl, heteroaryl, and $C_1$ to $C_8$ haloalkyl, α is an oxygen atom or a sulfur atom, $L^5$ is a bond, —(CH$_2$)v—, —C=C—, —CC—, —O—, or —S—, v is an integer from 0 to 2, β is —CH$_2$— or —(CH$_2$)$_2$—, γ is an oxygen atom or a sulfur atom, b is an integer from 0 to 3, d is an integer from 0 to 4, f, p, and w are independently an integer from 0 to 5, r is an integer from 0 to 7, and u is an integer from 0 to 4, or is (e) a member of (d) substituted with at least one substituent selected from the group consisting of $C_1$ to $C_6$ alkyl, $C_1$ to $C_8$ alkyloxy, $C_1$ to $C_8$ haloalkyloxy, $C_1$ to $C_8$ haloalkyl, aryl, and a halogen.

16. The compound of claim 1 wherein for $R_1$ the group $R_{11}$ is a substituted or unsubstituted carbocyclic radical selected from the group consisting of cycloalkyl, cycloalkenyl, phenyl, spiro[5.5]undecanyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (a):

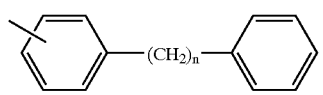

(a)

where n is a number from 1 to 8.

17. A substituted pyrrole compound represented by the formula (II), or a pharmaceutically acceptable salt, solvate, or prodrug derivative thereof;

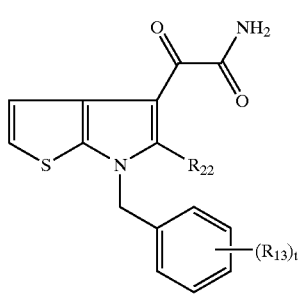

(II)

wherein;

R$_{22}$ is selected from hydrogen, methyl, ethyl, propyl, isopropyl, cyclopropyl, —F, —CF$_3$, —Cl, —Br, or —O—C$_3$;

R$_{13}$ is $C_2$–$C_8$ alkyl; and t is an integer from 0 to 5".

18. A substituted pyrrole compound represented by the formulae (C1), (C2), (C3), (C4), (C5), (C6), (C7), (C8), (C9), (C10), (C11), (C12), and (C13):

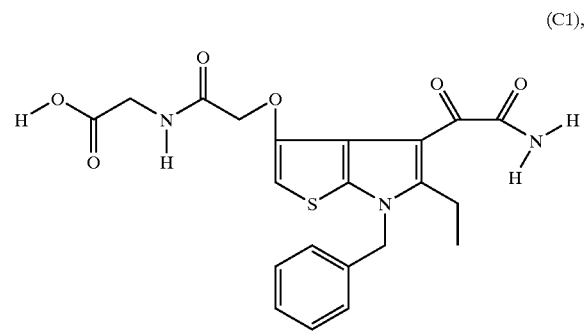

(C1),

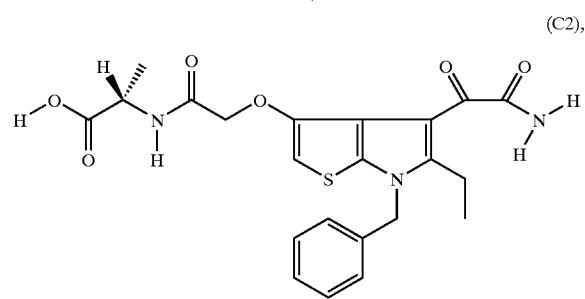

(C2),

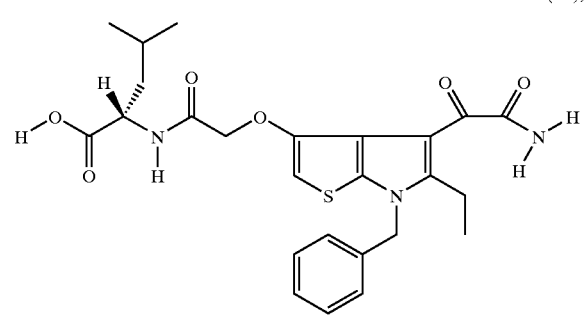

(C3),

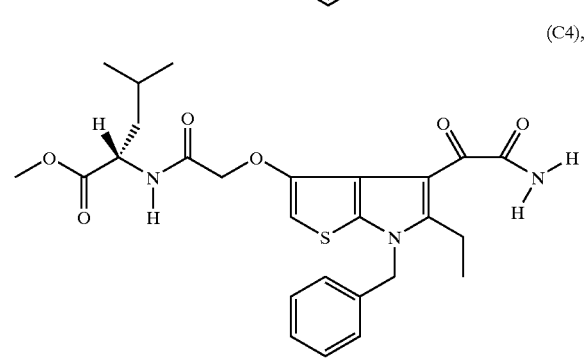

(C4),

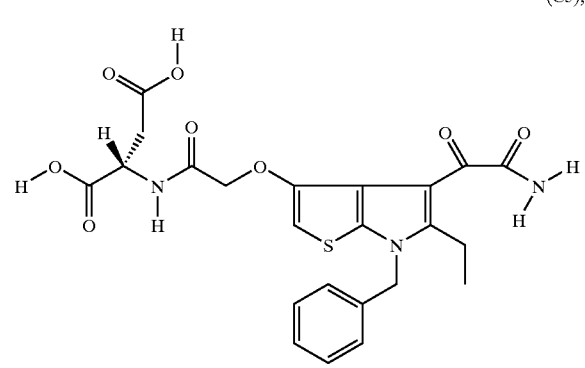

(C5), (C6),
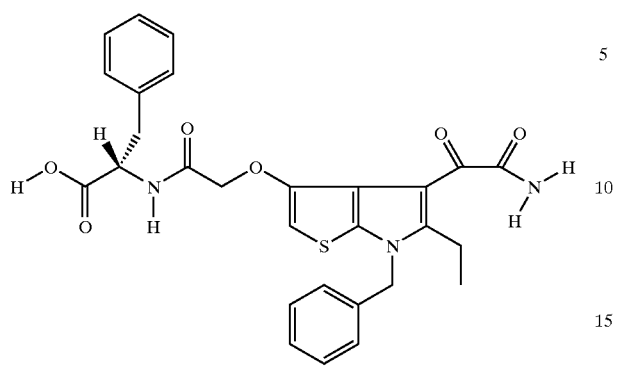

(C7),
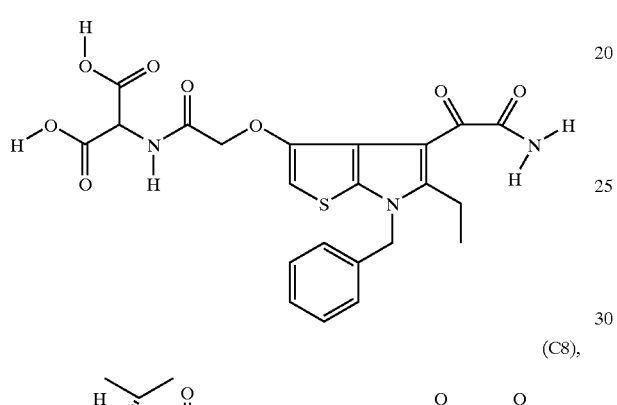

(C8),
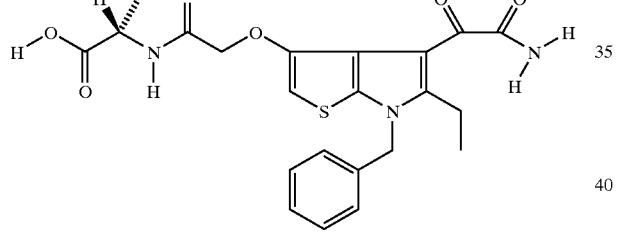

(C9),
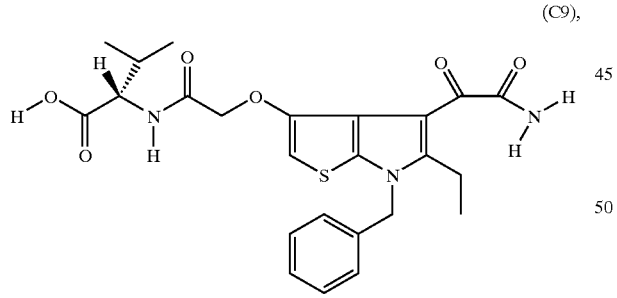

(C10),
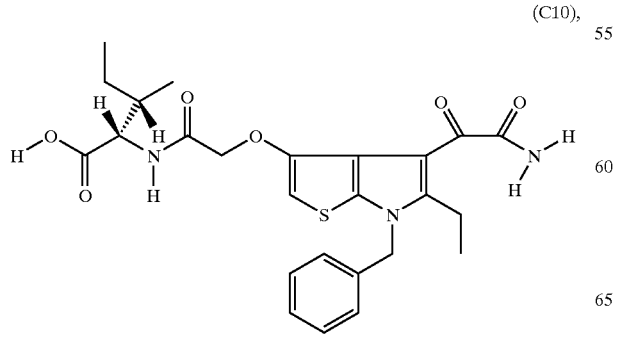

(C11),
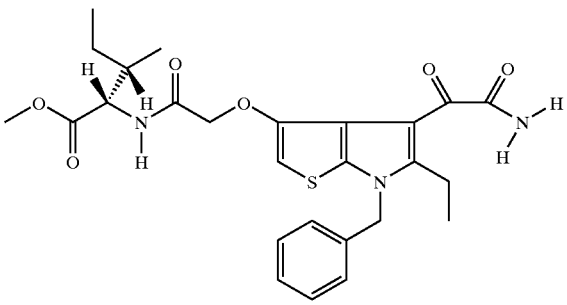

(C12),
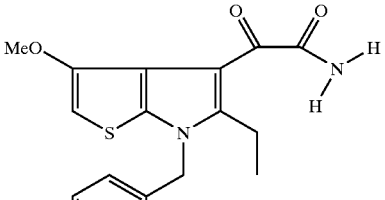

and (C13),
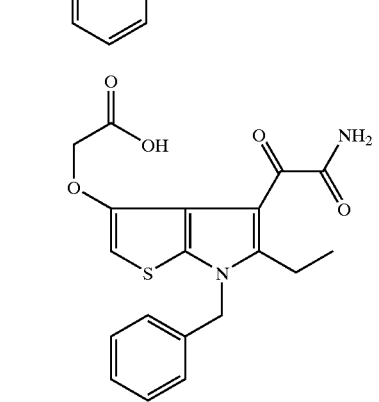

or a pharmaceutically acceptable salt or prodrug thereof.

19. A pharmaceutically formulation comprising a substituted pyrrole compound as claimed in claim 1 together with a pharmaceutically acceptable carrier or diluent therefor.

20. A method of inhibiting sPLA$_2$ mediated release of fatty acid which comprises contacting sPLA$_2$ with a therapeutically effective amount of a substituted pyrrole compound according to claim 1; and t is an integer from 0 to 5".

21. A method of treating a mammal to alleviate the pathological effects of Inflammatory Diseases; wherein the method comprises administering to said mammal a pharmaceutically effective amount of a compound according to claim 1.

22. A pharmaceutical formulation comprising an effective amount of the compound according to claim 1 for the treatment of Inflammatory Diseases.

23. A pharmaceutical formulation comprising an effective amount of the compound according to claim 1 useful as an inhibitor of sPLA$_2$ mediated release of fatty acid.

(C11),
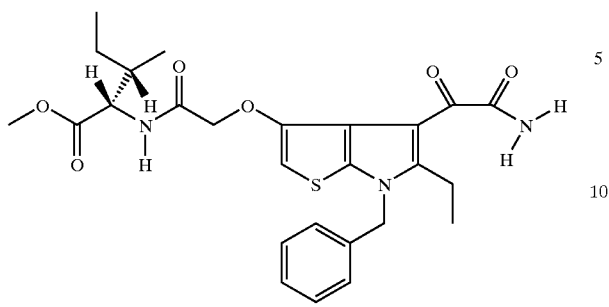
(C12),
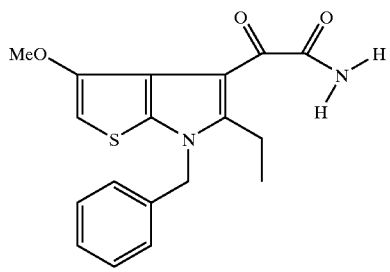
and
(C13),
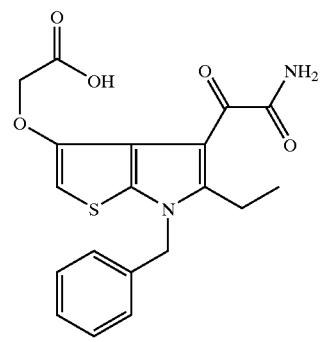
or a pharmaceutically acceptable salt or prodrug thereof.
* * * * *

UNITED STATES PATENT AND TRADEMARK OFFICE
CERTIFICATE OF CORRECTION

PATENT NO. : 6,730,694 B1  Page 1 of 1
APPLICATION NO. : 10/332480
DATED : May 4, 2004
INVENTOR(S) : Douglas Wade Beight et al.

Figure 2:
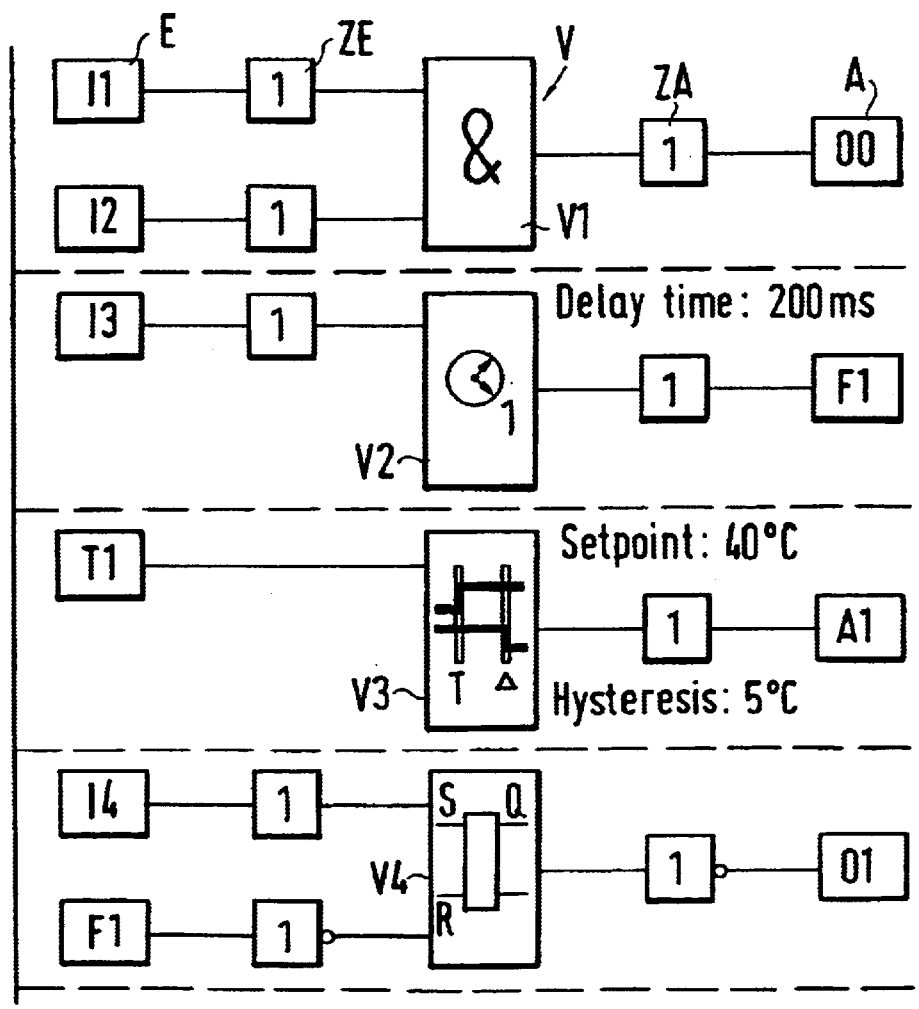

It is certified that error appears in the above-identified patent and that said Letters Patent is hereby corrected as shown below:

Drawings: Delete Fig. 1 and Fig. 2.

Signed and Sealed this

Twenty-ninth Day of January, 2008

JON W. DUDAS
*Director of the United States Patent and Trademark Office*